US012780872B2

(12) United States Patent
Vishwanatha et al.

(10) Patent No.: US 12,780,872 B2
(45) Date of Patent: Nov. 3, 2026

(54) CHARACTERIZATION OF INHIBITORY PEPTIDES (IPEPS) DERIVED FROM OF MIEN 1 PROTEIN SEQUENCE

(71) Applicant: The University of North Texas Health Science Cente, Fort Worth, TX (US)

(72) Inventors: Jamboor K. Vishwanatha, Fort Worth, TX (US); Amit Kumar Tripathi, Fort Worth, TX (US)

(73) Assignee: The University of North Texas Health Science Center, Fort Worth, TX (US)

( * ) Notice: Subject to any disclaimer, the term of this patent is extended or adjusted under 35 U.S.C. 154(b) by 255 days.

(21) Appl. No.: 18/237,368

(22) Filed: Aug. 23, 2023

(65) Prior Publication Data

US 2024/0409582 A1 Dec. 12, 2024

Related U.S. Application Data

(60) Provisional application No. 63/400,077, filed on Aug. 23, 2022.

(51) Int. Cl.

| | |
|---|---|
| ***C07K 7/06*** | (2006.01) |
| ***A61K 9/127*** | (2006.01) |
| ***A61K 9/51*** | (2006.01) |
| ***A61P 35/00*** | (2006.01) |
| *A61K 38/00* | (2006.01) |

(52) U.S. Cl.

CPC ................ *C07K 7/06* (2013.01); *A61K 9/127* (2013.01); *A61K 9/51* (2013.01); *A61P 35/00* (2018.01); *A61K 38/00* (2013.01)

(58) Field of Classification Search

CPC ........... C07K 7/06; A61P 35/00; A61K 9/127; A61K 9/51; A61K 38/00

See application file for complete search history.

(56) References Cited

U.S. PATENT DOCUMENTS

| | | | | |
|---|---|---|---|---|
| 3,773,919 | A | 11/1973 | Boswell et al. | |
| 7,294,596 | B2 | 11/2007 | Esmaeilzadeh | |
| 2002/0055478 | A1 * | 5/2002 | Faris | G01N 33/57484 435/6.14 |
| 2007/0081942 | A1 * | 4/2007 | Zauderer | A61P 35/00 424/1.49 |
| 2019/0085034 | A1 * | 3/2019 | Wooster | A61K 31/337 |
| 2020/0283745 | A1 * | 9/2020 | Lloyd | C12N 9/88 |

FOREIGN PATENT DOCUMENTS

| | | |
|---|---|---|
| EP | 133988 | 3/1985 |
| WO | WO93/15722 | 8/1993 |

OTHER PUBLICATIONS

Vasaikar, S.V., Deshmukh, A.P., den Hollander, P. et al. EMTome: a resource for pan-cancer analysis of epithelial-mesenchymal transition genes and signatures. Br J Cancer 124, 259-269 (2021). https://doi.org/10.1038/s41416-020-01178-9 (Year: 2021).*

Mak, M. P., et al. (2016). A Patient-Derived, Pan-Cancer EMT Signature Identifies Global Molecular Alterations and Immune Target Enrichment Following Epithelial-to-Mesenchymal Transition. Clinical cancer research 22(3), 609-620. https://doi.org/10.1158/1078-0432.CCR-15-0876 (Year: 2016).*

Sela, M. and Zisman, E. (1997), Different roles of D-amino acids in immune phenomena. The FASEB Journal, 11: 449-456. https://doi.org/10.1096/fasebj.11.6.9194525 (Year: 1997).*

Deng, T., Ge, H., He, H., Liu, Y., Zhai, C., Feng, L., & Yi, L. (2017). The heterologous expression strategies of antimicrobial peptides in microbial systems. Protein expression and purification, 140, 52-59. https://doi.org/10.1016/j.pep.2017.08.003 (Year: 2017).*

Golubovskaya V. M. (2010). Focal adhesion kinase as a cancer therapy target. Anti-cancer agents in medicinal chemistry, 10(10), 735-741. https://doi.org/10.2174/187152010794728648 (Year: 2010).*

Furuyama, K., Doi, R., Mori, T., Toyoda, E., Ito, D., Kami, K., Koizumi, M., Kida, A., Kawaguchi, Y., & Fujimoto, K. (2006). Clinical significance of focal adhesion kinase in resectable pancreatic cancer. World journal of surgery, 30(2), 219-226. https://doi.org/10.1007/s00268-005-0165-z (Year: 2006).*

Hsu, C. H., Shen, T. L., Chang, C. F., Chang, Y. Y., & Huang, L. Y. (2012). Solution structure of the oncogenic MIEN1 protein reveals a thioredoxin-like fold with a redox-active motif. PloS one, 7(12), e52292. https://doi.org/10.1371/journal.pone.0052292 (Year: 2012).*

Han et al., Protein and Peptide Letters, 2004 11(2): 1-8.

Ishida et al, Biopolymers 2004 76(1):69-82.

Sasaki et al, Biol. Pharm. Bull. 2004 27(2):244-7.

Pascal R et al, Meth. Enzymol. 2003 369:182-94.

Yoder N C and Kumar K, Chem. Soc. Rev. 2002 31(6):335-41.

Eppstein et al., Proc. Natl. Acad. Sci. USA, 82: 3688-92 (1985).

Dasgupta S, Wasson LM, Rauniyar N, Prokai L, Borejdo J, Vishwanatha JK. Novel gene C17orf37 in 17q12 amplicon promotes migration and invasion of prostate cancer cells. Oncogene. Aug. 13, 2009;28(32):2860-72. doi: 10.1038/onc.2009.145. Epub Jun. 8, 2009. PMID: 19503095; PMCID: PMC2726905.

Chang KS, Tsui KH, Lin YH, Hou CP, Feng TH, Juang HH. Migration and Invasion Enhancer 1 Is an NF-κB-Inducing Gene Enhancing the Cell Proliferation and Invasion Ability of Human Prostate Carcinoma Cells In Vitro and In Vivo. Cancers (Basel). Oct. 2, 2019;11(10):1486. doi: 10.3390/cancers11101486. PMID: 31581708; PMCID: PMC6826896.

Kpetemey, M., Dasgupta, S., Rajendiran, S. et al. MIEN1, a novel interactor of Annexin A2, promotes tumor cell migration by enhancing AnxA2 cell surface expression. Mol Cancer 14, 156 (2015). https://doi.org/10.1186/12943-015-0428-8.

Huang YB, Wang XF, Wang HY, Liu Y, Chen Y. Studies on mechanism of action of anticancer peptides by modulation of hydrophobicity within a defined structural framework. Mol Cancer Ther. Mar. 2011;10(3):416-26. doi: 10.1158/1535-7163.MCT-10-0811. Epub Jan. 20, 2011. PMID: 21252288.

Rajendiran S, Parwani AV, Hare RJ, Dasgupta S, Roby RK, Vishwanatha JK. MicroRNA-940 suppresses prostate cancer migration and invasion by regulating MIEN1. Mol Cancer. Nov. 19, 2014;13:250. doi: 10.1186/1476-4598-13-250. PMID: 25406943; PMCID: PMC4246551.

(Continued)

*Primary Examiner* — Christina M Marchetti Bradley
*Assistant Examiner* — Sachi Jauhari

(57) ABSTRACT

Embodiments of the invention are directed to inhibitors of MIEN1-mediated cancer signaling transduction pathways to inhibit cancer cell migration and their use as a cancer therapy. The inhibitors are a hexamer peptide and a heptamer peptide (therapeutic peptides) from the ITAM and the prenylation motif of MIEN1 that exhibit anti-cancer activity both in vitro and in vivo.

11 Claims, 15 Drawing Sheets

Specification includes a Sequence Listing.

(56) References Cited

OTHER PUBLICATIONS

Kpetemey M, Chaudhary P, Van Treuren T, Vishwanatha JK. MIEN1 drives breast tumor cell migration by regulating cytoskeletal-focal adhesion dynamics. Oncotarget. Aug. 23, 2016;7(34):54913-54924. doi: 10.18632/oncotarget.10798. PMID: 27462783; PMCID: PMC5342390.

Kushwaha PP, Gupta S, Singh AK, Kumar S. Emerging Role of Migration and Invasion Enhancer 1 (MIEN1) in Cancer Progression and Metastasis. Front Oncol. Sep. 4, 2019;9:868. doi: 10.3389/fonc.2019.00868. PMID: 31552186; PMCID: PMC6738349.

Tripathi, A. K., and Vishwanatha, J. K. (2023) Abstract 2184: Short Peptides derived from MIEN1 and their analogs exhibit anti-cancer activity in breast and prostate cancer cells Cancer Research 83, 2184-2184 10.1158/1538-7445.Am2023-2184.

* cited by examiner

| Peptide Name | Peptide Sequence | Cell Line | $IC_{50}$ (μM) | Cell type | Tumor/non-tumor |
|---|---|---|---|---|---|
| LA-6 | LASAVK | MDA-MB-231 | >600 | Breast Cancer | tumorigenic |
| **LA3IK** | **LAIAVK** | | 223.6±5.62 | | |
| SR-8 | SRPPCVIL | | 528.28±4.57 | | |
| CR-8 | CRPPCVIL | | >600 | | |
| **RP-7** | **RPPCVIL** | | 139.03±8.41 | | |

FIG. 2

| Peptide Name | Peptide Sequence | Cell Line | $IC_{50}$ (μM) | Cell type | Tumor/non-tumor |
|---|---|---|---|---|---|
| LA-6 | LASAVK | DU-145 | >600 | Prostate Cancer | Tumorigenic |
| **LA3IK** | **LAIAVK** | | 335.7±3.09 | | |
| SR-8 | SRPPCVIL | | >600 | | |
| CR-8 | CRPPCVIL | | >600 | | |
| **RP-7** | **RPPCVIL** | | 120.72±7.08 | | |

FIG. 3

| Peptide Name | Peptide Sequence | Cell Line | $IC_{50}$ (μM) | Cell type | Tumor/non-tumor |
|---|---|---|---|---|---|
| LA-6 | LASAVK | NIH-3T3 | >600 | Fibroblasts | Non-Tumorigenic |
| **LA3IK** | **LAIAVK** | | >600 | | |
| SR-8 | SRPPCVIL | | >600 | | |
| CR-8 | CRPPCVIL | | >600 | | |
| **RP-7** | **RPPCVIL** | | 221±6.23 | | |

FIG. 4

CHARACTERIZATION OF INHIBITORY PEPTIDES (IPEPS) DERIVED FROM OF MIEN 1 PROTEIN SEQUENCE

RELATED APPLICATION

This Application claims priority to U.S. Provisional Application Ser. No. 63/400,077 filed Aug. 23, 2022, which is incorporated herein by reference in its entirety.

STATEMENT REGARDING FEDERALLY FUNDED RESEARCH

None.

REFERENCE TO SEQUENCE LISTING

A sequence listing required by 37 CFR 1.821-1.825 is being submitted electronically with this application. The sequence listing is incorporated herein by reference. The sequence listing that is contained in the file named "UNTHSC-P0001US" which is 28 KB (as measured in Microsoft Windows®) and was created on 8/23/2023.

FIELD OF THE INVENTION

Embodiments of the invention are directed generally to the field of molecular biology and medicine, particularly to the field of peptide therapies for cancer.

BACKGROUND

Chemotherapy is one of the classical approaches to treat cancer where a cytotoxic agent is delivered to cancer cells. The main problem with conventional chemotherapy is the development of chemoresistance which is one of the major causes of therapeutic failure in breast cancer patients. One way to control cancer is to target key proteins involved in cancer progression. Peptides from structurally important regions of proteins involved in cancer progression is one option for identification of peptides with anti-cancer properties. These peptides can act as a dominant-negative version of the parent protein and can inhibit the related protein-mediated signaling pathways. Further, peptides possess many advantages such as small size, ease of synthesis and modification, biocompatibility, and the capability of penetrating tumor tissue.

One such cancer progression protein is the Migration and Invasion Enhancer 1 (MIEN1) protein. MIEN1 was previously identified as C17orf37 by Dasgupta et al. to play a crucial role in migration and invasion of prostate cancer cells. MIEN1 is a membrane-anchored protein located in the 17q12 region of the human chromosome. The MIEN1 gene encodes a 115 amino acid/12 KDa molecular weight protein. The MIEN1 protein is predominantly present in the cytosol with little plasma membrane-associated expression. The biological function of MIEN is to increase cell migration by inducing filopodia formation at the leading edge of migrating cells. Overexpression of MIEN1 was initially identified in breast and colon cancer. MIEN1 expression positively correlates with the grade and stage of breast cancer compared with minimal expression in normal tissues. Thus, the differential expression of MIEN1 in normal vs. cancer cells makes it a candidate tumor biomarker. Work by Dasgupta et al. and Chang et al. showed that MIEN1 activates NF-kB in breast cancer and in prostate cancer cells. The approaches for modulating MIEN1 is primarily confined to identifying micro-RNAs to regulate MIEN1 gene expression and its effects on cancer cells.

There is an unmet need for inhibitory molecules specific to MIEN1. Thus, there is a need for additional therapies for treating various cancers and in particular additional therapies for inhibiting migration and invasion of cancers.

SUMMARY

The Inventors have identified a solution to the problem of treating cancers and in particular providing inhibitors of the downstream cancer signaling pathways of MIEN1 to inhibit cancer cell migration. The solution is a short hexamer peptide and/or heptamer peptide (therapeutic peptides) from the ITAM and the prenylation motif of MIEN1 that exhibit anti-cancer activity both in vitro and in vivo. Interestingly the peptides target the MIEN1 induced signaling pathway which exhibits cancerous activities in breast cancer cells, prostate cancer cells, and other cancers.

Therapeutic MIEN1 peptides showed selective cytotoxicity against MDA-MB-231 breast cancer and DU-145 prostate cancer cells. The therapeutic peptides inhibit the cancer signal transduction pathways and exert anti-cancer properties. The therapeutic peptides inhibited the migration and invasion in highly metastatic human breast cancer cell line MDA-MB-231. Expression of Epithelial-Mesenchymal Transition (EMT) genes, which play a key role in cancer progression, are inhibited by treatment with the MIEN1 therapeutic peptides. The therapeutic peptides also inhibit tumor growth in athymic nude mice and were well tolerated by mice at three times the experimental dose, demonstrating cancer cell-selectivity and non-cytotoxicity to normal cells and animal models.

The therapeutic peptides are LA3IK having the amino acid sequence LAIAVK (SEQ ID NO:4) and RP-7 having the amino acid sequence RPPCVIL (SEQ ID NO:7). In certain aspects any peptide can have 0, 1, 2, 3, 4, 5, 6, or 7 D amino acids.

Certain embodiments are directed to compositions including one or more therapeutic peptides, a first therapeutic peptide having or consisting of or consisting essentially of a six amino acid sequence of LAIAVK (SEQ ID NO:4), and a second therapeutic peptide having or consisting of or consisting essentially of seven amino acid sequence of RPPCVIL (SEQ ID NO:7). The therapeutic peptide or peptides can further comprise an amino terminal modification, a carboxy terminal modification, or amino terminal modification and carboxy terminal modification. In certain aspects, a therapeutic peptide or peptides can further comprise a heterologous peptide. The heterologous peptide can be covalently or non-covalently coupled to the first therapeutic peptide or the second therapeutic peptide. The heterologous peptide(s) can be an amino terminal amino acid sequence, carboxy terminal amino acid sequence, or amino terminal amino acid sequences and carboxy terminal amino acid sequences. In certain aspects the heterologous amino acid sequence can be a targeting sequence. The compositions of the invention can be included in or complexed to a delivery vehicle. The delivery vehicle can be a nanoparticle or a liposome.

Other embodiments are directed to methods for treating cancer comprising administering a composition comprising a six amino acid peptide having an amino acid sequence of LAIAVK (SEQ ID NO:4), a seven amino acid peptide having an amino acid sequence of RPPCVIL (SEQ ID NO:7), or a six amino acid peptide having an amino acid sequence of LAIAVK (SEQ ID NO:4) and a seven amino acid peptide having an amino acid sequence of RPPCVIL (SEQ ID NO:7). In certain aspects the amino acids can be L, D, or L and D amino acids. In certain aspects the cancer is breast cancer, colorectal cancer, prostate cancer, gastric cancer, ovarian cancer, squamous cell carcinoma, or non-small cell lung cancer. The therapeutic peptide(s) can be administered in combination with at least a second anti-cancer agent. The at least second anti-cancer agent can be a chemotherapy drug or a cancer immunotherapy drug. In certain aspects the therapeutic peptide(s) and second anti-cancer agent are comprised in the same composition. The therapeutic peptide(s) can be administered before; during; after; before and during; before and after; during and after; or before, during and after administration of the second anti-cancer agent.

Certain embodiments are directed to methods for inhibiting cancer or cancer cell migration in a subject comprising administering a composition comprising a six amino acid peptide having an amino acid sequence of LAIAVK (SEQ ID NO:4), a seven amino acid peptide having an amino acid sequence of RPPCVIL (SEQ ID NO:7), or a six amino acid peptide having an amino acid sequence of LAIAVK (SEQ ID NO:4) and a seven amino acid peptide having an amino acid sequence of RPPCVIL (SEQ ID NO:7) to a subject in need thereof. A cancer cell can be, but is not limited to, breast cancer cells, colorectal cancer cells, prostate cancer cells, gastric cancer cells, ovarian cancer cells, squamous cell carcinoma cells, or non-small cell lung cancer cells.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa. Furthermore, compositions and kits of the invention can be used to achieve methods of the invention.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. As used herein, the terms "comprises," "comprising," "includes," "including," "has," "having," "contains", "containing," "characterized by" or any other variation thereof, are intended to encompass a non-exclusive inclusion, subject to any limitation explicitly indicated otherwise, of the recited components. For example, a chemical composition and/or method that "comprises" a list of elements (e.g., components or features or steps) is not necessarily limited to only those elements (or components or features or steps) but may include other elements (or components or features or steps) not expressly listed or inherent to the chemical composition and/or method.

As used herein, the transitional phrases "consists of" and "consisting of" exclude any element, step, or component not specified. For example, "consists of" or "consisting of" used in a claim would limit the claim to the components, materials or steps specifically recited in the claim except for impurities ordinarily associated therewith (i.e., impurities within a given component). When the phrase "consists of" or "consisting of" appears in a clause of the body of a claim, rather than immediately following the preamble, the phrase "consists of" or "consisting of" limits only the elements (or components or steps) set forth in that clause; other elements (or components) are not excluded from the claim as a whole.

As used herein, the transitional phrases "consists essentially of" and "consisting essentially of" are used to define a chemical composition and/or method that includes materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between "comprising" and "consisting of".

Other objects, features, and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

FIG. 2. IC50 determination of peptides in MDA-MB-231 cells.

FIG. 3. IC50 determination of peptides in DU-145 cells.

FIG. 4. IC50 determination of peptides in NIH-3T3 cells.

DESCRIPTION

Figures 1A, 1B, 1C:
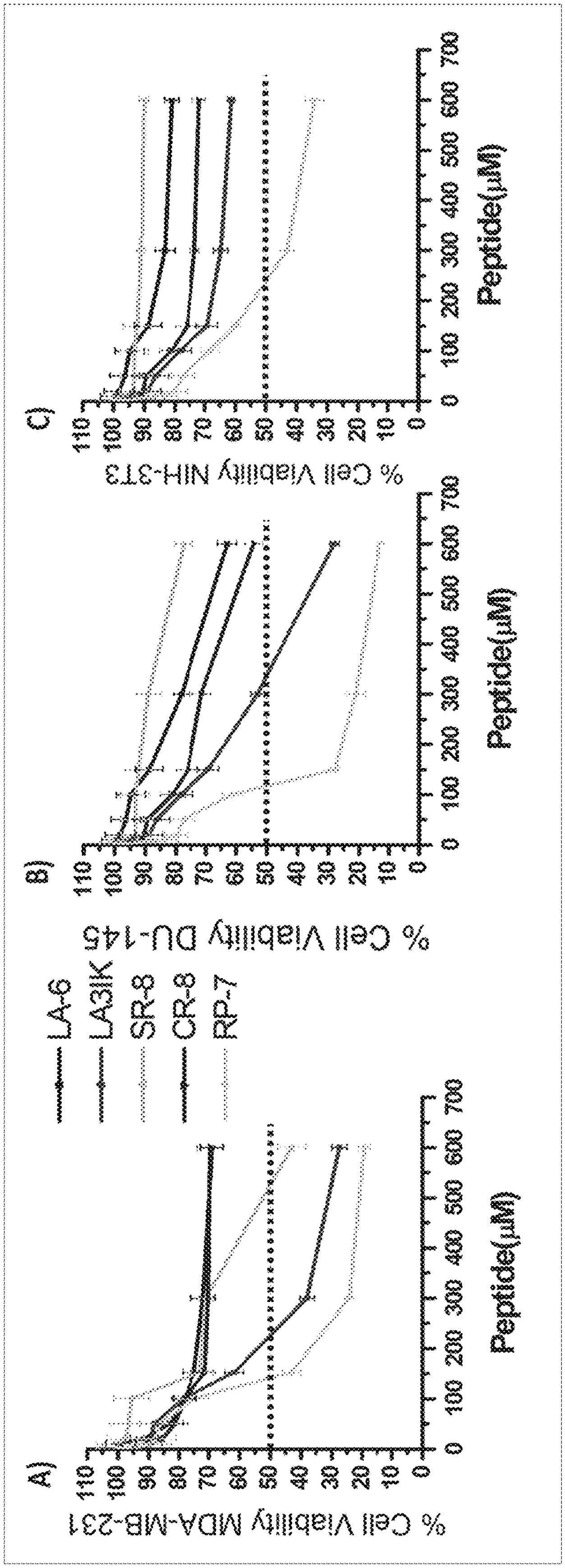
FIG. 1A-1C. in vitro Antiproliferative Effects of MIEN-1 derived peptides and it's analogs on (A) MDA-MB-231 cells, (B) DU-145 cells and (C) NIH-3T3 cells. LA-6=LASAVK (SEQ ID NO:3), LA3IK=LAIAVK (SEQ ID NO:4), SR-8=SRPPCVIL (SEQ ID NO:5), CR-8=CRPPCVIL (SEQ ID NO:6), and RP-7=RPPCVIL (SEQ ID NO:7).
Figure 5:
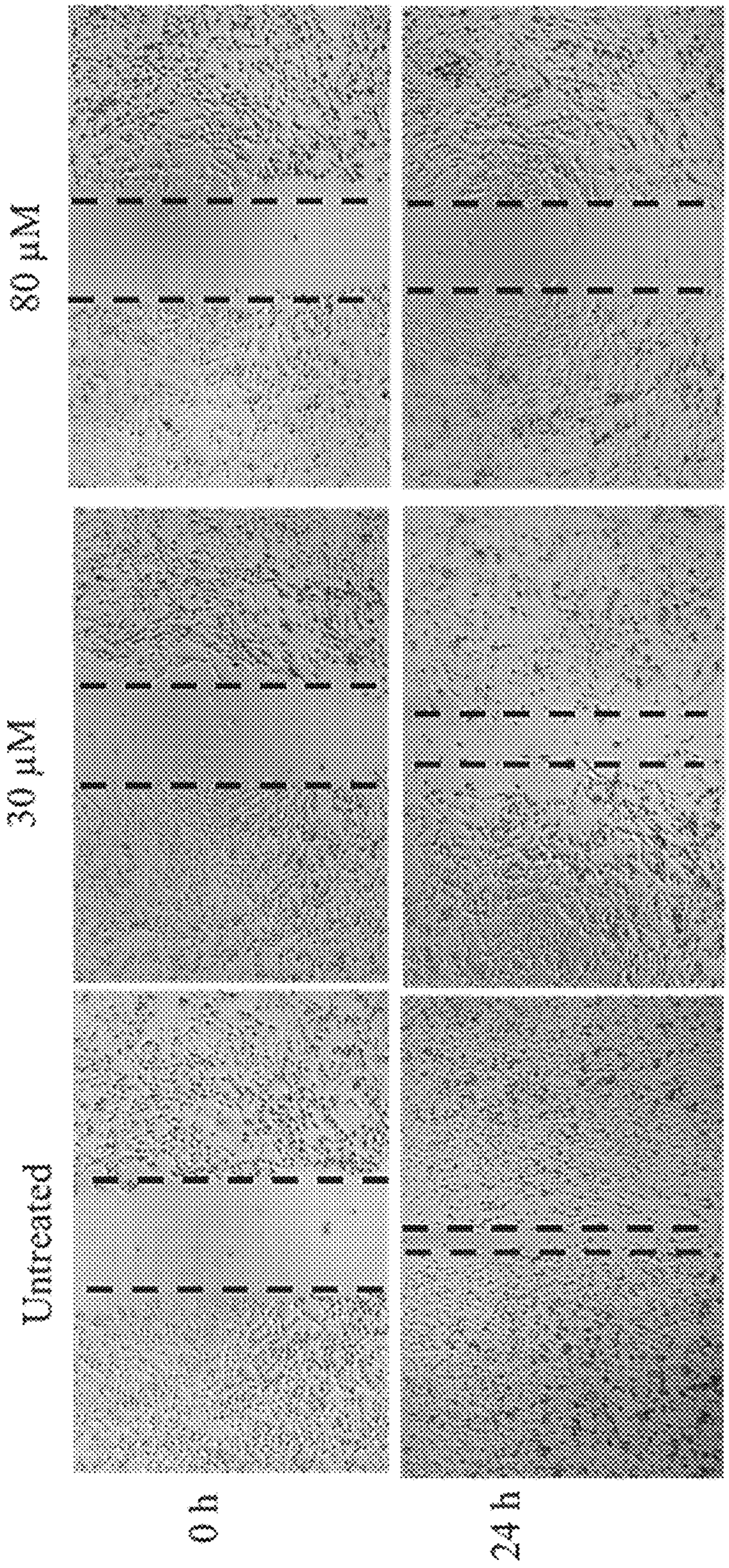
FIG. 5. Dose-dependent inhibition of cell migration of MDA-MB-231 in response to LA3IK (LAIAVK (SEQ ID NO:4)).
Figure 6:
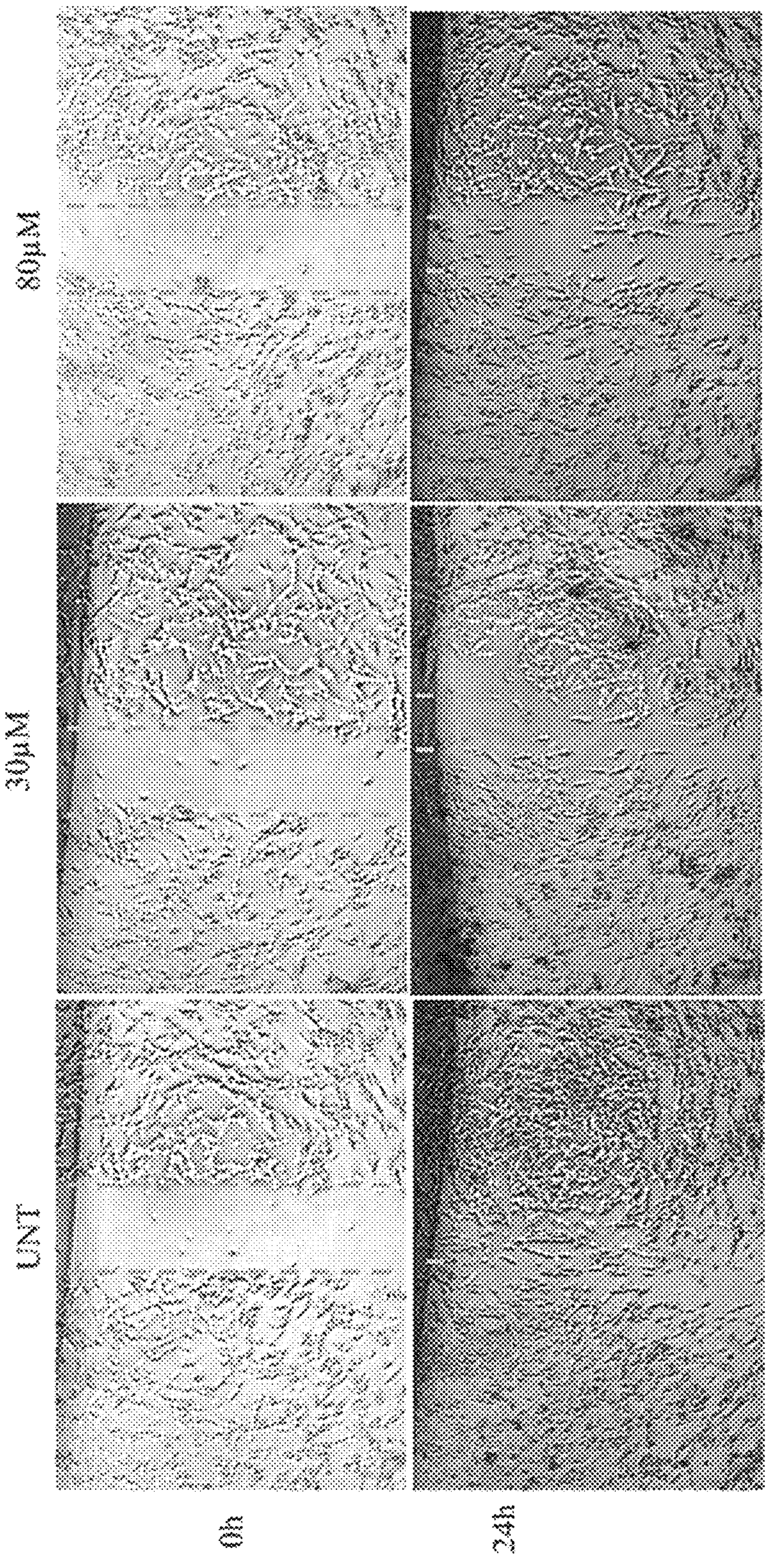
FIG. 6. Dose-dependent inhibition of cell migration of MDA-MB-231 in response to RP-7 (RPPCVIL (SEQ ID NO:7)).
Figure 7:
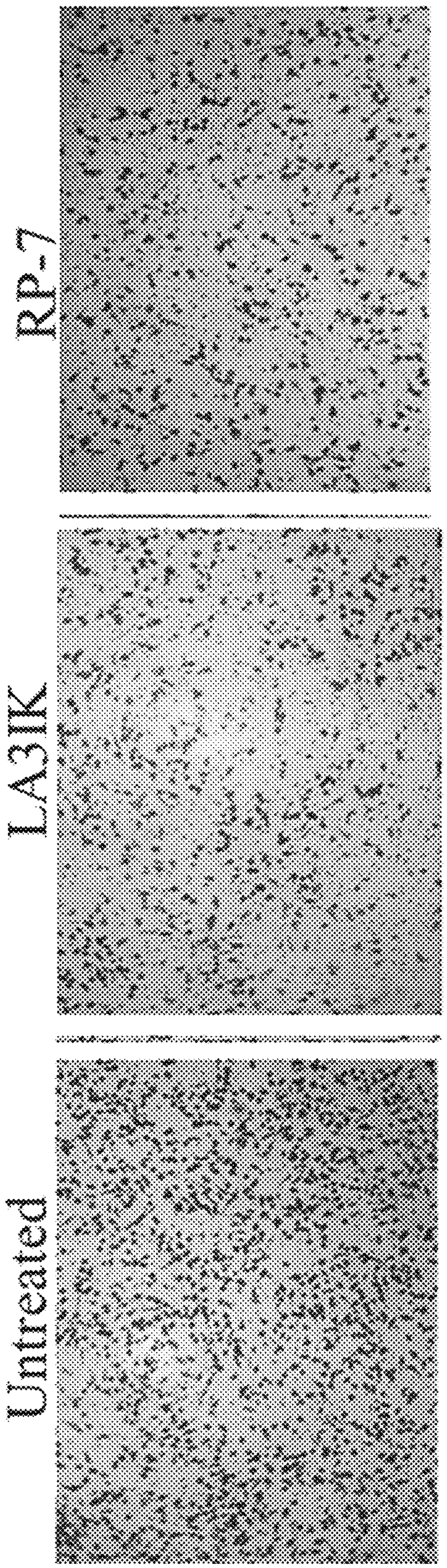
FIG. 7. Inhibition of invasive capacities of MDA-MB-231 cells against LA3IK (LAIAVK (SEQ ID NO:4) and RP-7 (RPPCVIL (SEQ ID NO:7) after 24 hours of treatment at 80 μm.
Figure 8A:
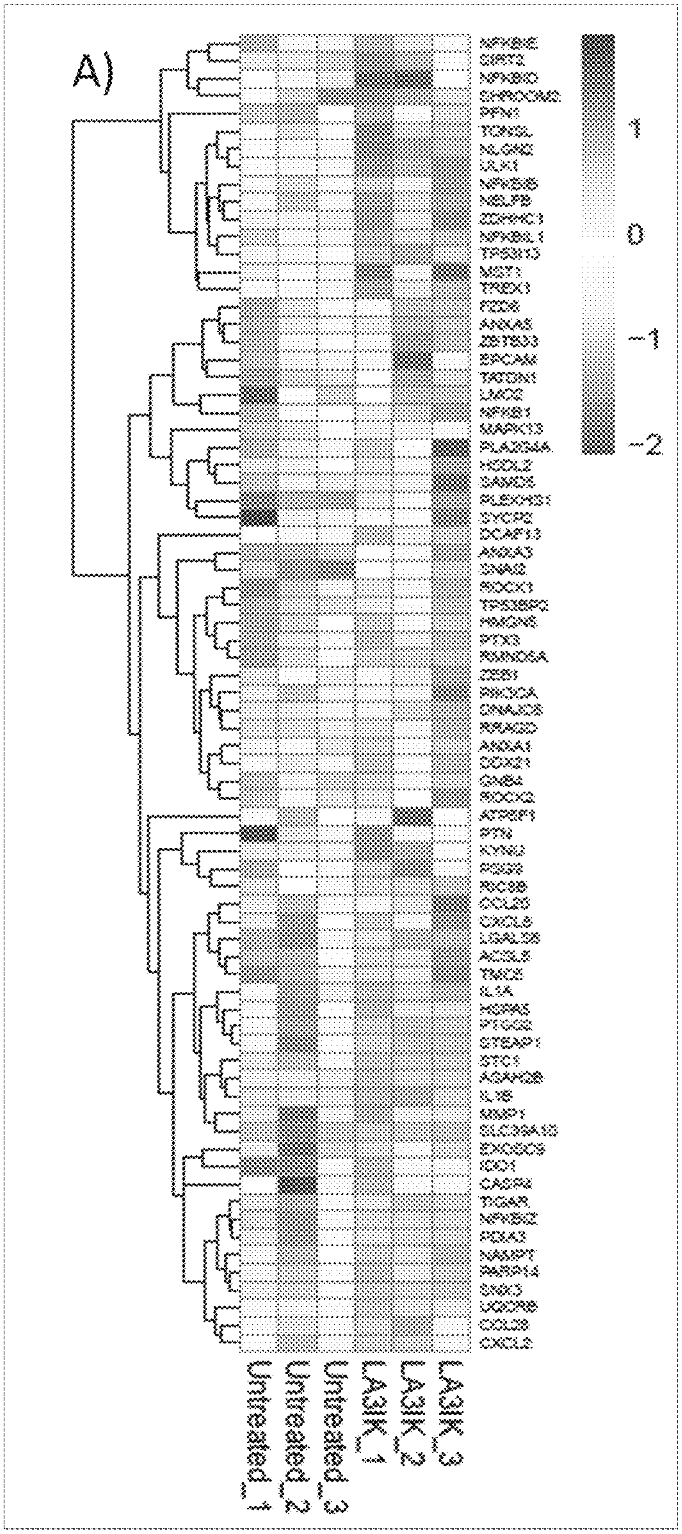
FIG. 8A-8D: Changes in the transcriptome of MDA-MB-231 cells after peptide treatment. (A) LA3IK treatment inhibited genes responsible for migration and cancer progression and upregulated genes responsible for tumor suppression and EMT. Three biologically independent RNA samples of MDA-MB-231 cells per group were sequenced. (B) Volcano plot shows the distribution of differentially expressed genes for LA3IK-treated MDA-MB-231 cells. (C) and (D) show the heatmap and volcano plot of selected genes after 48 h exposure to RP-7.
Figures 8B, 8C, 8D:
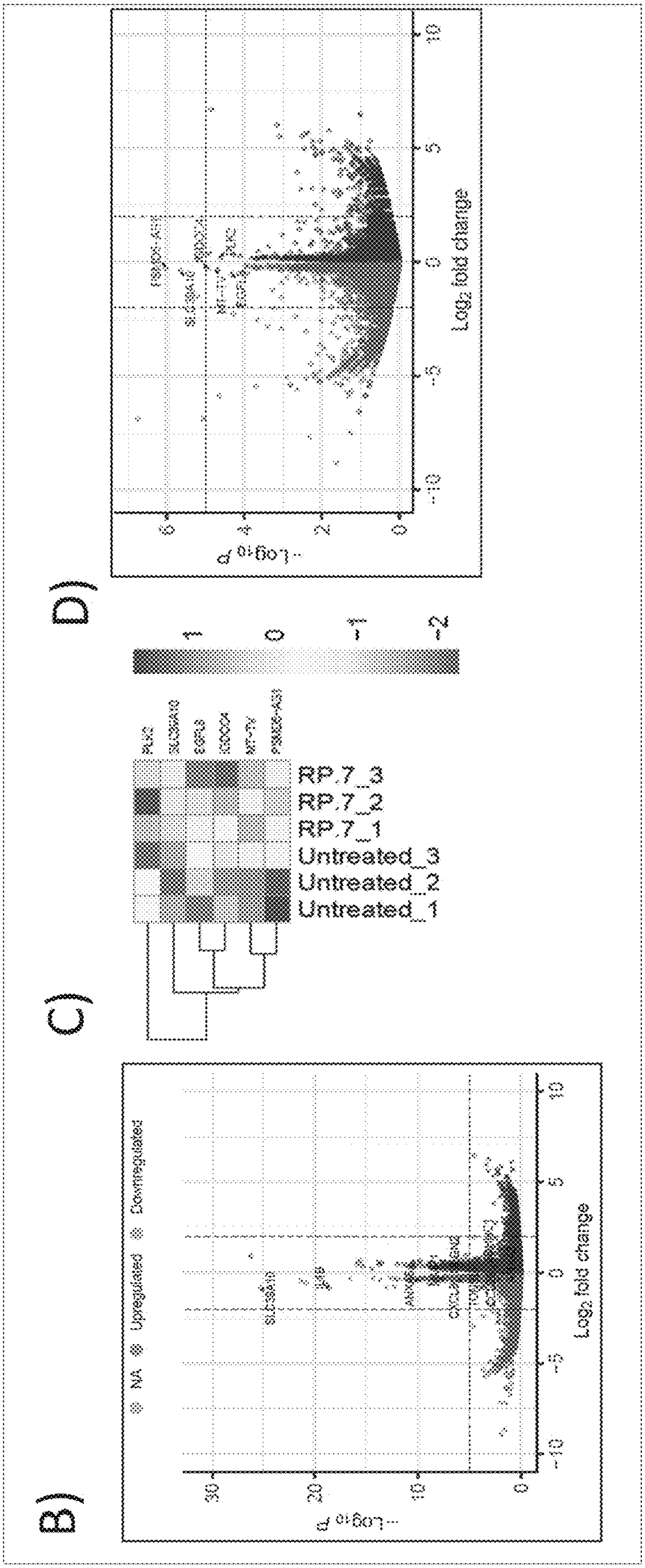
Figure 9:
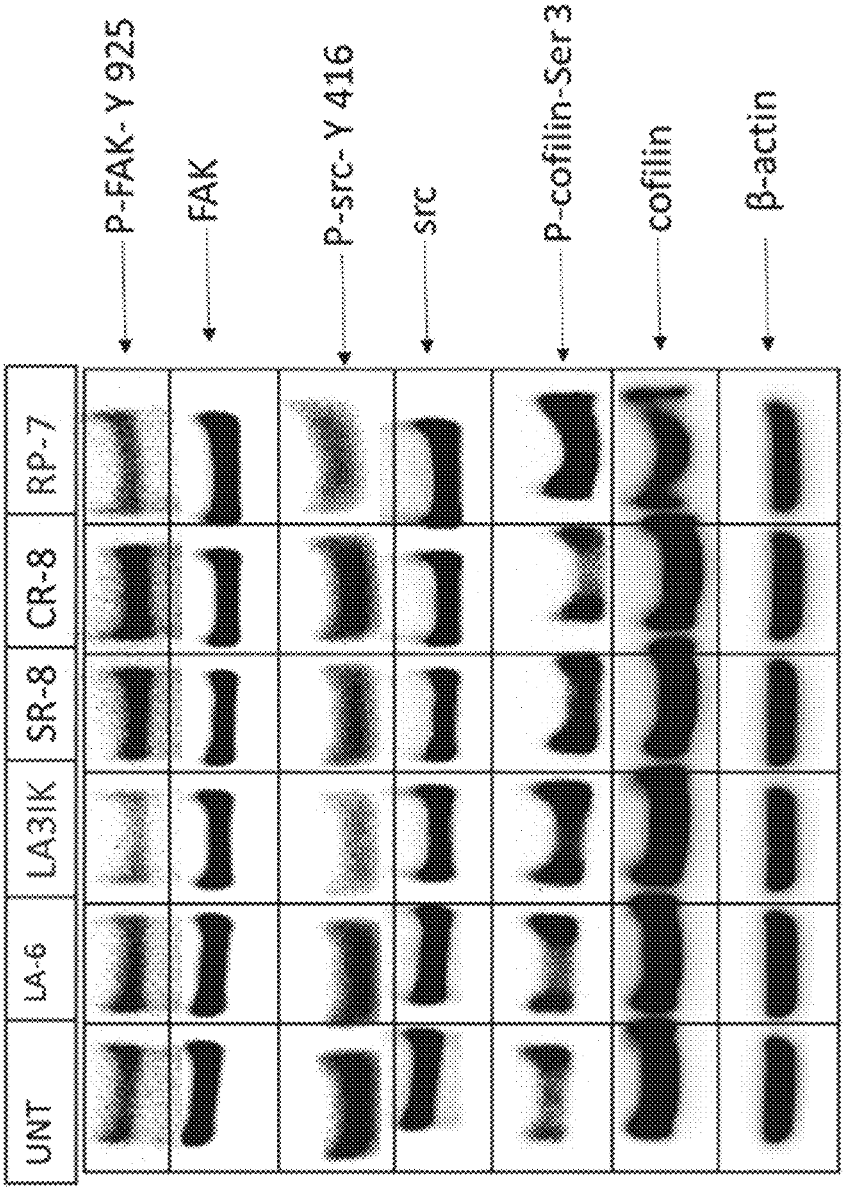
FIG. 9. Changes in Protein Expression. MDA-MB-231 cells treated with peptides at 48 hours. Whole cell lysates were analyzed by Western blot using 3-actin as a loading control.
Figure 10:
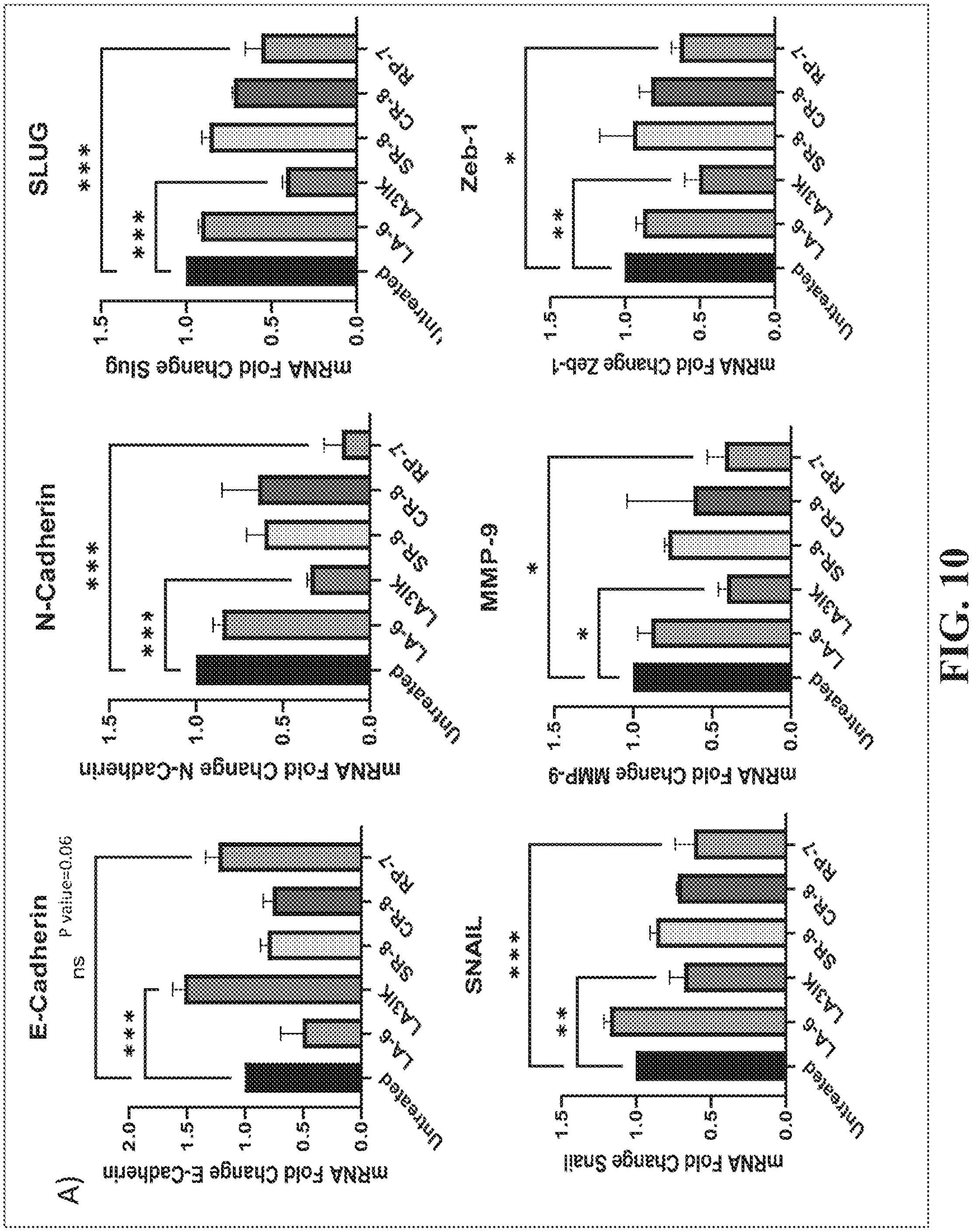
FIG. 10. Graphs representing the decrease/increase in mRNA fold change of genes involved in EMT epithelial to mesenchymal transition (EMT) in DU-145 prostate cancer cells assay, E-cadherin, N-Cadherin, SLUG, SNAIL, MMP-9, and Zeb-1 (*p value<0.05, p<value 0.01, *p<value 0.01.
Figures 11A, 11B, 11C, 11D, 11E, 11F:
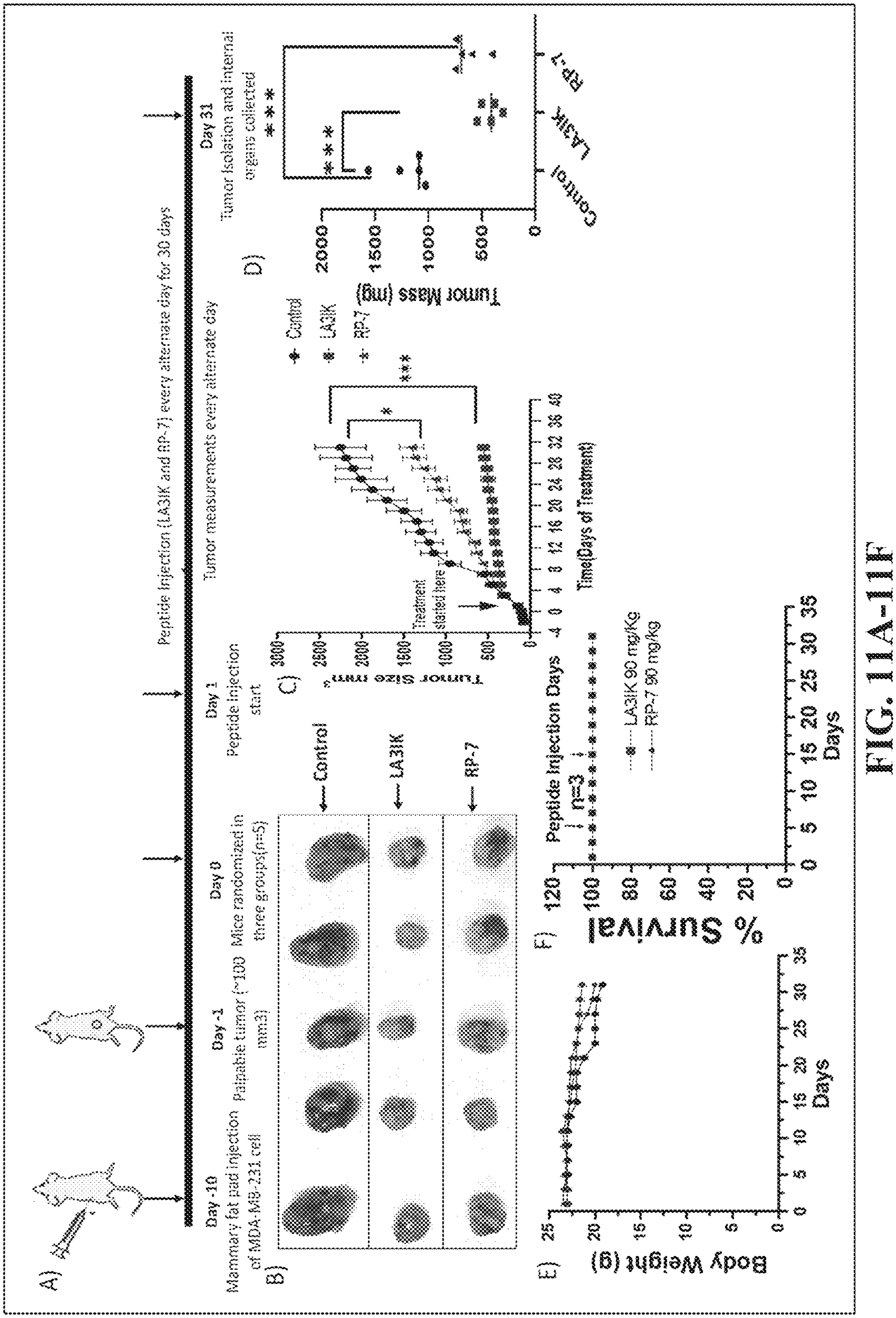
FIG. 11A-11F. in vivo efficacy of LA3IK and RP-7 in nude mice bearing MDA-MB-231 orthotropic tumors: (A) Timeline of the in vivo experiment. MDA-MB-231 cells were implanted orthotopically into the second thoracic mammary fat pad of nude mice (n=5). After 10 days, tumor-bearing mice were grouped and treated with LA3IK and RP-7 by peritumoral injection at a dose of 30 mg/kg every alternate day. The control mice received vehicle only. (B) At the end of the experiments, representative tumors were removed and photographed. (C) The tumor growth did not decrease in the control group, whereas the LA3IK and RP-7 decreased tumor growth significantly. The Tumor sizes were measured by a digital caliper and shown as mean volume±SD every alternate day for 30 days. Unpaired t-test, LA3IK (30 mg/Kg), ***P<0.001 and RP-7 (30 mg/Kg), *p<0.05. The statistical analysis was performed on GraphPad Prism 9.4.0. (D) Individual tumor weight of each mouse in the LA3IK and RP-7 treated group in comparison with the control group after 30 days of treatment (E) The mice were monitored for changes in body weights as a surrogate marker for toxicity. Body weight loss was observed in the control group after $20^{th}$ day of the experiment. (F) in vivo toxicity of LA3IK and RP-7 Athymic nude mice were injected intraperitoneally with three times the experimental peptide dose (90 mg/Kg of body weight) on Day 5 and Day 15. All mice (n=3) were alive after 30 days.

The following discussion is directed to various embodiments of the invention. The term "invention" is not intended to refer to a particular embodiment(s) or otherwise limit the scope of the disclosure. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be an example of that embodiment, and not intended to imply that the scope of the disclosure, including the claims, is limited to that embodiment.

I. MIGRATION AND INVASION ENHANCER 1 (MIEN1) PROTEIN

MIEN1 is a tumor-specific target protein which is responsible for the migration and invasion of various types of cancers. The protein is overexpressed in the human breast, prostate, colorectal, gastric, ovarian, squamous cell carcinoma and non-small cell lung cancer (NSCLC) as compared to the normal cells, which makes it an excellent therapeutic target. Studies on MIEN1 have also shown its role in promoting drug resistance in some cancer types. Besides this, the small size of MIEN1 protein is also one of the challenges associated with therapeutic drug targeting of the protein. The present invention is directed to the design of small inhibitory peptides from the MIEN1 protein sequence, which inhibit the migration and invasion of cancer cells in vitro and in vivo.

The gene encoding MIEN1 is found to be abundantly expressed in various tumor tissues and functions as a critical regulator of tumor cell migration and invasion promoting systemic metastases. Previous studies have identified post-translational modifications by isoprenylation at the C-terminal tail of MIEN1 to favor its translocation to the inner leaflet of plasma membrane and its function as a membrane-bound adapter molecule. The protein is involved in negative regulation of apoptotic process, positive regulation of cell migration, and positive regulation of filopodium assembly. MIEN1 has been found in several cellular components/compartments including the centriolar satellite, cytosol, and nucleoplasm.

There are two isoforms of MIEN1 protein. Isoform 1 having the amino acid sequence MSGEPGQTSVAPP-PEEVEPGSGVRIVVEYCEPCGFEATYLELA-SAVKEQYPGIEIESRLGG TGAFEIEINGQLVFSK-LENGGFPYEKDLIEAIRRASNGETLEKITNSRPPCVIL (SEQ ID NO:1, accession NP_115715.3). MIEN 1 isoform 1 is a 115 amino acid protein with a disordered domain from amino acid 1 to amino acid 21, an acetylation site at amino acid 2, and a selenoprotein domain from amino acid 25 to amino acid 95. Isoform 2 has the amino acid sequence MSGEPGQTSVAPPPEEVEPGSGVRIVVEY-CEPCGFEATYLELASAVKEQYPGIEIESRLGG TGA-FEIEINGQLVFSKLENGGFPYEKDVSIYSVGRTS-WSPYPNSASSCHSTPLAH (SEQ ID NO:2, accession NP_001317135.1). MIEN1 isoform 2 is a 116 amino acid protein with a disordered domain from amino acid 1 to amino acid 21, an acetylation site at amino acid 2, and a selenoprotein domain from amino acid 25 to amino acid 89. Isoforms 1 and 2 differ in the carboxy terminal 8 amino acids of isoform 1 as compared to the carboxy terminal 9 amino acids of isoform 2.

The Inventors have identified two essential motifs within the MIEN1 protein sequence, the ITAM motif and CVIL motif. In the current invention the Inventors have designed short therapeutic peptide fragments within these motifs. The newly designed peptides and their analogs demonstrate an ability to inhibit the migration and invasion of MDA-MB-231 breast cancer cells in vitro. This discovery is important because it is a novel approach to target MIEN1. By inhibiting the cell migration and invasion of tumor cells from the primary site, cancer progression can be checked or inhibited.

TABLE 1

MIEN1 derived peptides

| Sequence | Peptide Name: | Znet | % Hydrophobicity | Molecular Weight |
|---|---|---|---|---|
| LASAVK (SEQ ID NO: 3) | LA-6 | +1 | 66.67% | 587.71 |
| LAIAVK (SEQ ID NO: 4) | LA3IK | +1 | 83.33% | 613.79 |
| ILEAIRR (SEQ ID NO: 22) | IL-7 | +1 | 57.14% | 870.05 |
| SRPPCVIL (SEQ ID NO: 5) | SR-8 | +1 | 62.5% | 884.1 |
| CRPPCVIL (SEQ ID NO: 6) | CR-8 | +1 | 62.5% | 900.17 |
| RPPCVIL (SEQ ID NO: 7) | RP-7 | +1 | 71.43 | 838.09 |

By using a peptide-based approach, the small inhibitory peptide fragments can easily gain access to the grooves and concavities in the MIEN1 and bind those pockets inhibiting the function or interactions of the protein. The size of the inhibitory peptides minimizes effects on normal cells and reduce cytotoxicity or unwanted off-target activity. Modifications of the therapeutic peptides can enhance their biostability, such as synthesizing the D-isomers of active inhibitory peptides. Also, therapeutic peptides can be encapsulated in a delivery vehicle, such as nanoparticles, to make them even more specific.

The incorporation of non-natural amino acids, including synthetic non-native amino acids, substituted amino acids, or one or more D-amino acids into the peptides (or other components of the composition, with exception for protease recognition sequences) is desirable in certain situations. D-amino acid-containing peptides exhibit increased stability in vitro or in vivo compared to L-amino acid-containing forms. Thus, the construction of peptides incorporating D-amino acids can be particularly useful when greater in vivo or intracellular stability is desired or required. More specifically, D-peptides are resistant to endogenous peptidases and proteases, thereby providing better oral transepithelial and transdermal delivery of linked drugs and conjugates, improved bioavailability of membrane-permeant complexes, and prolonged intravascular and interstitial lifetimes when such properties are desirable. Additionally, D-peptides cannot be processed efficiently for major histocompatibility complex class II-restricted presentation to T helper cells and are therefore less likely to induce humoral immune responses in the whole organism. Peptide(s) and peptide(s) conjugates can therefore be constructed using D-isomer forms of bioactive peptides.

As used herein, a "conservative substitution" in a polypeptide or peptide is the replacement of an amino acid with another amino acid that has the same net electronic charge and approximately the same size and shape. Amino acids with aliphatic or substituted aliphatic amino acid side chains have approximately the same size when the total number of carbon and heteroatoms in their side chains differs by no more than about four. They have approximately the same shape when the number of branches in their side chains differs by no more than one. Amino acids with phenyl or substituted phenyl groups in their side chains are considered to have about the same size and shape. Listed below are five groups of amino acids. Replacing an amino acid in a polypeptide or peptide with another amino acid from the same group results in a conservative substitution: Group I: glycine, alanine, valine, leucine, isoleucine, serine, threonine, cysteine, and non-naturally occurring amino acids with C1-C4 aliphatic or C1-C4 hydroxyl substituted aliphatic side chains (straight chained or monobranched). Group II: glutamic acid, aspartic acid and non-naturally occurring amino acids with carboxylic acid substituted C1-C4 aliphatic side chains (unbranched or one branch point). Group III: lysine, ornithine, arginine and non-naturally occurring amino acids with amine or guanidino substituted C1-C4 aliphatic side chains (unbranched or one branch point). Group IV: glutamine, asparagine and non-naturally occurring amino acids with amide substituted C1-C4 aliphatic side chains (unbranched or one branch point). Group V: phenylalanine, phenylglycine, tyrosine and tryptophan.

As used herein, a "highly conservative substitution" in a peptide is the replacement of an amino acid with another amino acid that has the same functional group in the side chain and nearly the same size and shape. Amino acids with aliphatic or substituted aliphatic amino acid side chains have nearly the same size when the total number of carbon and heteroatoms in their side chains differs by no more than two. They have nearly the same shape when they have the same number of branches in their side chains. Examples of highly conservative substitutions include valine for leucine, threonine for serine, aspartic acid for glutamic acid and phenylglycine for phenylalanine. Examples of substitutions which are not highly conservative include alanine for valine, alanine for serine and aspartic acid for serine.

In certain aspects a peptide described herein (e.g., SEQ ID NO:4 and/or SEQ ID NO:7) can include 1, 2, 3, 4, or more conservative or highly conservative substitutions at one or more amino acid selected from position 1, 2, 3, 4, 5, 6 of SEQ ID NO:4 or 1, 2, 3, 4, 5, or more conservative or highly conservative substitutions at one or more amino acid selected from position 1, 2, 3, 4, 5, 6, and/or 7 of SEQ ID NO:7.

The therapeutic peptide(s) may comprise amino acids with one or more modifications including, but not limited to, myristoylation, palmitoylation, isoprenylation, glypiation, lipoylation, acylation, acetylation, aklylation, methylation, glycosylation, malonylation, hydroxylation, iodination, nucleotide addition, oxidation, phosphorylation, adenylylation, propionylation, succinylation, sulfation, selenoylation, biotinylation, pegylation, deimination, deamidation, eliminylation, and carbamylation. The therapeutic peptide may comprise one or more amino acids conjugated to one or more small molecules, for example a drug. In some embodiments, the therapeutic peptide comprises one or more non-natural amino acids. In some embodiments, the therapeutic peptide comprises 1, 2, 3, 4, 5, 6, 7 or more non-natural amino acids. In certain embodiments the non-natural amino acid is at position 1, 2, 3, 4, 5, 6, and/or 7 of SEQ ID NO:4 or SEQ ID NO:7. In some embodiments, the therapeutic peptide comprises one or more amino acids substitutions. A modification in a peptide may affect 1, 2, 3, 4 or more non-contiguous or contiguous amino acids of therapeutic peptides, as compared to the original therapeutic peptide. In certain embodiments the peptides are D-isomer peptides.

As used herein, the term "amino acid" is used in its broadest sense and includes naturally occurring amino acids as well as non-naturally occurring amino acids, including amino acid analogs and derivatives. The term "Naturally-occurring amino acid" is used herein to refer to the twenty amino acids that occur in nature in L form, which include alanine, cysteine, aspartate, glutamate, phenylalanine, glycine, histidine, isoleucine; lysine, leucine, methionine, asparagine, proline, glutamine, arginine, serine, threonine, valine, tryptophan, and tyrosine, or any derivative thereof produced through a naturally-occurring biological process or pathway. The term "Non-naturally-occurring amino acid" is used herein to refer to an amino acid other than a naturally-occurring amino acid, which can be synthesized or "man-made", and including a derivative thereof, whether produced synthetically or via a biological process or pathway. Non-naturally occurring amino acids include, without limitation, D amino acids, amino acids containing unnaturally substituted side chains, e.g., methyl-Arg, cyclic amino acids, diamino acids, 3-amino acids, homo amino acids. Non-naturally-occurring or unnatural amino acids may be characterized by novel backbone and side chain structures and are widely available from commercial reagent suppliers, such as Sigma-Aldrich. See also a broad literature on such structures including, without limitation, Han and Viola, *Protein Pept. Lett.* 2004 11(2):104-14; Ishida et al, *Biopolymers* 2004 76(1):69-82; Sasaki et al, *Biol. Pharm. Bull.* 2004 27(2):244-7; Pascal et al, *Meth. Enzymol.* 2003 369: 182-94; Yoder and Kumar, *Chem. Soc. Rev.* 2002 31(6):335-41; and Ager, *Curr. Opin. Drug Discov. Devel.* 2002 5(6): 892-905, among others, all of which are incorporated herein by reference. This term does not encompass those derivatives which fall within the definition of a "naturally-occurring amino acid". Thus, in one embodiment of compounds of this invention, one or more of the amino acids in the peptide may be in L form, while others may be in D form. Chemically synthesized compounds having properties known in the art to be characteristic of amino acids are also included in this definition.

In certain embodiments, the therapeutic peptide is a fusion peptide that is linked at the N- or C-terminus to a second peptide or polypeptide. The second polypeptide may be, for example, another therapeutic peptide or a detectable label. In other embodiments, the peptide comprises a linker interposed between the therapeutic peptide and the second peptide or polypeptide sequence. Linkers are discussed in greater detail in the specification below.

Furthermore, the therapeutic peptides set forth herein may comprise a heterologous sequence of any number of additional amino acid residues at either the N-terminus or C-terminus of the amino acid sequence. For example, there may be an amino acid sequence of about 3 to about 1,000 or more amino acid residues at either the N-terminus, the C-terminus, or both the N-terminus and C-terminus of the amino acid sequence that includes a therapeutic peptide.

The therapeutic peptide may include the addition of an antibody epitope or other tag, to facilitate identification, targeting, and/or purification of the polypeptide. The use of 6×His (hexahistidine) and GST (glutathione S transferase) as tags is well known. Inclusion of a cleavage site at or near the fusion junction will facilitate removal of the heterologous polypeptide. Other amino acid sequences that may be included in the therapeutic peptide include functional domains, such as active sites from enzymes such as a hydrolase, glycosylation domains, cellular targeting moiety, or transmembrane region(s). The therapeutic peptide may further include one or more additional tissue- or cell-targeting moieties.

The therapeutic peptide may possess deletions and/or substitutions of amino acids relative to the native sequence. Sequences with amino acid substitutions are contemplated, as are sequences with a deletion, and sequences with a deletion and a substitution. In some embodiments, the therapeutic peptide may further include insertions or added amino acids.

Substitutional or replacement variants typically contain the exchange of one amino acid for another at 1, 2, 3, or 4 sites within the therapeutic peptide and may be designed to modulate one or more properties of the therapeutic peptide, particularly to increase its stability, efficacy, or specificity. Substitutions of this kind may or may not be conservative substitutions. It is specifically contemplated that one or more conservative substitutions or highly conservative substitutions may be included as embodiments. In some embodiments, such substitutions are specifically excluded. Furthermore, in additional embodiments, substitutions that are not conservative are employed in variants.

The therapeutic peptide sequence may be structurally equivalent to the native counterpart. For example, the therapeutic peptide sequence forms the appropriate structure and conformation for binding targets, proteins, or peptide segments.

Polypeptide/peptide can be made by any technique known to those of skill in the art, including (i) the expression of proteins, polypeptides, or peptides through standard molecular biological techniques, (ii) the isolation of polypeptide/peptide from natural sources, or (iii) the chemical synthesis of polypeptides/peptides. The nucleotide sequences encoding the polypeptides/peptides can be found in the recognized computerized databases. One such database is the National Center for Biotechnology Information's GenBank and GenPept databases (on the World Wide Web at ncbi.nlm.nih.gov/). All or part of the coding regions for these genes may be amplified and/or expressed using the techniques disclosed herein or as would be known to those of ordinary skill in the art.

Therapeutic peptides and modified therapeutic peptides can be synthesized by solid phase peptide synthesis (e.g., BOC or FMOC) method, by solution phase synthesis, or by other suitable techniques including combinations of the foregoing methods. The BOC and FMOC methods, which are established and widely used, are described in Merrifield, *J. Am. Chem. Soc:* 88:2149 (1963); Meienhofer, *Hormonal Proteins and Peptides*, C. H. Li, Ed., Academic Press, 1983, pp. 48-267; and Barany and Merrifield, in *The Peptides*, Gross and Meienhofer, Eds., Academic Press, New York, 1980, pp. 3-285. Methods of solid phase peptide synthesis are described in Merrifield, *Science,* 232: 341 (1986); Carpino and Han, *J. Org. Chem.*, 37: 3404 (1972); and Gauspohl et al, *Synthesis, J:* 315 (1992)).

It also will be understood that amino acid and nucleic acid sequences may include additional residues, such as additional N- or C-terminal amino acids, or 5' or 3' nucleic acid sequences, respectively, and yet still be essentially as set forth in one of the sequences disclosed herein, so long as the sequence meets the criteria set forth above, including the maintenance of biological protein activity. The addition of terminal sequences particularly applies to nucleic acid sequences that may, for example, include various non-coding sequences flanking either of the 5' or 3' portions of the coding region.

The therapeutic peptide described herein may be fused, conjugated, or operatively linked to a label. As used herein, the term "label" intends a directly or indirectly detectable compound or composition that is conjugated directly or indirectly to the composition to be detected, e.g., polynucleotide or protein to generate a "labeled" composition. The term also includes sequences conjugated to the polynucleotide that will provide a signal upon expression of the inserted sequences, such as green fluorescent protein (GFP) and the like. The label may be detectable by itself (e.g., radioisotope labels or fluorescent labels) or, in the case of an enzymatic label, may catalyze chemical alteration of a substrate compound or composition which is detectable. The labels can be suitable for small scale detection or more suitable for high-throughput screening. As such, suitable labels include, but are not limited to radioisotopes, fluorochromes, chemiluminescent compounds, dyes, and proteins, including enzymes.

Examples of luminescent labels that produce signals include but are not limited to bioluminescence and chemiluminescence. Detectable luminescence response generally comprises a change in, or an occurrence of, a luminescence signal. Suitable methods and luminophores for luminescently labeling assay components are known in the art and described for example in Haugland, Richard P. (1996) *Handbook of Fluorescent Probes and Research Chemicals* (6th ed.). Examples of luminescent probes include, but are not limited to, aequorin and luciferases.

Examples of suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, Cascade Blue™, and Texas Red. Other suitable optical dyes are described in the Haugland, Richard P. (1996) *Handbook of Fluorescent Probes and Research Chemicals* (6th ed.).

In another aspect, the fluorescent label is functionalized to facilitate covalent attachment. Suitable functional groups include but not are limited to isothiocyanate groups, amino groups, haloacetyl groups, maleimides, succinimidyl esters, and sulfonyl halides, all of which may be used to attach the fluorescent label to a second molecule. The choice of the functional group of the fluorescent label will depend on the site of attachment to either a linker, the agent, the marker, or the second labeling agent.

Attachment of the fluorescent label may be either directly to a peptide or alternatively, can by via a linker. Suitable binding pairs for use in indirectly linking the fluorescent label to the intermediate include, but are not limited to, biotin/avidin or biotin/streptavidin.

It is contemplated that in composition embodiments, there is between about 0.001 mg and about 10 mg of total peptide per ml. Thus, the concentration of peptide in a composition can be about, at least about or at most about 0.001, 0.010, 0.050, 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 50, 100 μg/ml or mg/ml or more (or any range derivable therein).

II. METHODS FOR TREATMENT

Certain embodiments are directed to method of treating a subject by administering an effective amount of one or more therapeutic peptide(s) described herein or a composition comprising one or more therapeutic peptide(s). In certain aspects the subject has, is suspected of having, or at risk of developing cancer or a metastatic cancer.

An "effective amount" is the quantity of the therapeutic peptide described herein that results in an improved clinical outcome of the condition being treated with the therapeutic peptide compared with the absence of treatment. The amount of the therapeutic peptide administered will depend on the degree, severity, and type of the disease or condition, the amount of therapy desired, and the release characteristics of the pharmaceutical formulation. It will also depend on the subject's health, size, weight, age, sex and tolerance to drugs.

Typically, the therapeutic peptide is administered for a sufficient period of time to achieve the desired therapeutic effect. Typically, from about 1 μg per day to about 1 mg per day of therapeutic peptide (preferably from about 5 μg per day to about 100 μg per day) is administered to the subject in need of treatment, especially for a local means of administration. Therapeutic peptide(s) can also be administered at a dose of from about 0.1 mg/kg/day to about 15 mg/kg/day, with from about 0.2 mg/kg/day to about 3 mg/kg/day being preferred, especially for systemic means of administration. Typical dosages for the therapeutic peptide of the invention are also 5 to 500 mg/day, preferably 25 to 250 mg/day, especially for systemic means of administration.

"Treating" means that following a period of administering the therapeutic peptide or composition comprising a therapeutic peptide, a beneficial therapeutic and/or prophylactic result is achieved, which can include a decrease in the severity of symptoms or delay in or inhibition of the onset of symptoms, increased longevity and/or more rapid or more complete resolution of the disease or condition, or other improved clinical outcome as measured according to the site that is being observed or the parameters measured for a particular disease or disorder. "Reducing the risk" refers to decreasing the probability of developing a disease, disorder or medical condition, in a subject, wherein the subject is, for example, a subject who is at risk for developing the disease, disorder or condition.

A. Administration

The disclosed therapeutic peptides can be administered by any suitable route, locally (e.g., topically) or systemically, including, for example, by parenteral administration.

Parenteral administration can include, for example, intratumoral, intramuscular, intravenous, subcutaneous, or intraperitoneal injection or vascular administration, and can also include transdermal patch and implanted slow-release devices such as pumps. Topical administration can include, for example, creams, gels, ointments or aerosols. Respiratory administration can include, for example, inhalation or intranasal drops. For certain indications, it is advantageous to inject or implant the therapeutic peptide directly to the treatment site (e.g., a tumor). The therapeutic peptide can be advantageously administered in a sustained release formulation. The therapeutic peptide can be administered chronically, wherein the peptide derivative is administered over a long period of time (at least 60 days, but more typically, for at least one year), at intervals or by a continuous delivery method, to treat a chronic or recurring disease or condition.

B. Formulation

The therapeutic peptide can be administered to the subject in an acceptable pharmaceutical carrier as part of a pharmaceutical composition. The formulation of the pharmaceutical composition will vary according to the route of administration selected. Suitable pharmaceutical carriers may contain inert ingredients which do not interact with the compound. The carriers should be biocompatible, i.e., non-toxic, non-inflammatory, non-immunogenic and devoid of other undesired reactions at the administration site.

Examples of pharmaceutically acceptable carriers include, for example, saline, aerosols, commercially available inert gels, or liquids supplemented with albumin, methyl cellulose or a collagen matrix. Standard pharmaceutical formulation techniques can be employed, such as those described in *Remington's Pharmaceutical Sciences*, Mack Publishing Company, Easton, PA. Other suitable pharmaceutical carriers include those described in U.S. Pat. No. 7,294,596, the entire teaching of which is incorporated herein by reference.

The compositions used in the methods of the present invention can additionally comprise a pharmaceutical carrier in which the therapeutic peptide is dissolved or suspended. Examples of pharmaceutically acceptable carriers include, for example, saline, aerosols, commercially available inert gels, or liquids supplemented with albumin, methyl cellulose or a collagen matrix. Typical of such formulations are gels. Gels are comprised of a base selected from an oleaginous base, water, or an emulsion-suspension base. To the base is added a gelling agent that forms a matrix in the base, increasing its viscosity to a semisolid consistency. Examples of gelling agents are hydroxypropyl cellulose, acrylic acid polymers, and the like. The active ingredients are added to the formulation at the desired concentration at a point preceding addition of the gelling agent or can be mixed after the gelation process.

The term "pharmaceutically acceptable" as used herein means approved by a regulatory agency of the Federal or a state government or listed in the U.S. Pharmacopeia or other generally recognized pharmacopeia for use in animals, and more particularly in humans The term "carrier" refers to a diluent, adjuvant, excipient, or vehicle with which an active ingredient is administered. Such pharmaceutical carriers can be liquids, such as water and oils, including those of petroleum, animal, vegetable or synthetic origin, such as peanut oil, soybean oil, mineral oil, sesame oil and the like. Non-limiting examples of the pharmaceutical carriers include: saline, gum acacia, gelatin, starch paste, talc, keratin, colloidal silica, urea, nanoparticle, liposome, cationic liposome, or micelle etc. In addition, other excipients can be used.

Injectable delivery formulations may be administered intravenously or directly at the site in need of treatment. The injectable carrier may be a viscous solution or gel.

Delivery formulations include physiological saline, bacteriostatic saline (saline containing about 0.9% mg/mL benzyl alcohol), phosphate-buffered saline, Hank's solution, Ringer's-lactate, or liquids supplemented with albumin, methyl cellulose, or hyaluronic acid. Injectable matrices include polymers of poly(ethylene oxide) and copolymers of ethylene and propylene oxide (see Cao et al, *J. Biomater. Sci* 9:475 (1998) and Sims et al, *Plast Reconstr. Surg.* 98:843 (1996), the entire teachings of which are incorporated herein by reference).

Methods for encapsulating compositions (such as in a coating of hard gelatin or cyclodextran) are known in the art (Baker, et al, *Controlled Release of Biological Active Agents*, John Wiley and Sons, 1986).

Ointments are typically prepared using an oleaginous base, e.g., containing fixed oils or hydrocarbons, such as white petrolatum or mineral oil, or an absorbent base, e.g., consisting of an absorbent anhydrous substance or substances, for example anhydrous lanolin. Following formation of the base, the active ingredients are added in a desired concentration.

Creams generally comprise an oil phase (internal phase) containing typically fixed oils, hydrocarbons, and the like, such as waxes, petrolatum, mineral oil, and the like, and an aqueous phase (continuous phase), comprising water and any water-soluble substances, such as added salts. The two phases are stabilized by use of an emulsifying agent, for example, a surface-active agent, such as sodium lauryl sulfate; hydrophilic colloids, such as acacia colloidal clays, beegum, and the like. Upon formation of the emulsion, the active ingredients are added in the desired concentration.

Gels contain a base selected from an oleaginous base, water, or an emulsion-suspension base, as previously described. To the base is added a gelling agent which forms a matrix in the base, increasing its viscosity to a semisolid consistency. Examples of gelling agents are hydroxypropyl cellulose, acrylic acid polymers, and the like. The active ingredients are added to 710 the formulation at the desired concentration at a point preceding addition of the gelling agent.

Therapeutic peptide(s) and/or additional therapeutic agents described herein may be formulated for delivery in a delivery vehicle. The delivery vehicle can provide local concentration of the product (e.g., bolus, depot effect) and/or increased stability or half-life. The therapeutic peptide(s) and/or additional therapeutic agents may be formulated with particulate preparations of polymeric compounds such as polylactic acid, polyglycolic acid, etc., as well as agents such as a biodegradable matrix, injectable microspheres, microcapsular particles, microcapsules, bioerodible particles beads, liposomes, and implantable delivery devices that provide for the controlled or sustained release of the agent. Techniques for formulating such sustained- or controlled-delivery means are known and a variety of polymers have been developed and used for the controlled release and delivery of drugs. Such polymers are typically biodegradable and biocompatible. Polymer hydrogels, including those formed by complexation of enantiomeric polymer or polypeptide segments, and hydrogels with temperature or pH sensitive properties, may be desirable for providing drug depot effect because of the mild and aqueous conditions involved in trapping bioactive protein agents. See, for example, the description of controlled release porous polymeric microparticles for the delivery of pharmaceutical compositions in WO 93/15722.

Suitable materials for this purpose include polylactides (see, e.g., U.S. Pat. No. 3,773,919), polymers of poly-(a-hydroxycarboxylic acids), such as poly-D-(−)-3-hydroxybutyric acid (EP 133,988A), copolymers of L-glutamic acid and gamma ethyl-L-glutamate (Sidman et al., *Biopolymers,* 22: 547-556 (1983)), poly(2-hydroxyethyl-methacrylate) (Langer et al., *J. Biomed. Mater. Res.,* 15: 167-277 (1981), and Langer, Chem. Tech., 12: 98-105 (1982)), ethylene vinyl acetate, or poly-D(−)-3-hydroxybutyric acid. Other biodegradable polymers include poly(lactones), poly(acetals), poly(orthoesters), and poly(orthocarbonates). Sustained-release compositions also may include liposomes, which may be prepared by any of several methods known in the art (see, e.g., Eppstein et al., *PNAS* USA, 82: 3688-92 (1985)). The carrier itself, or its degradation products, should be nontoxic in the target tissue and should not further aggravate the condition. This may be determined by routine screening in animal models of the target disorder or, if such models are unavailable, in normal animals.

Therapeutic peptide(s) and/or additional therapeutic agents may be microencapsulated.

Delivery Vehicles. A delivery vehicle for use in the compositions and with the methods herein may include a nanoparticle. A delivery vehicle can have diameters from about 40 nm, 50 nm, 60 nm, 70 nm, 80 nm, 90 nm, 100 nm, 110 nm, 120 nm, 130 nm, 140 nm, 150 nm, 160 nm, 170 nm, 180 nm, 190 nm, 200 nm, 210 nm, 220 nm, 230 nm, 240 nm, 250 nm, or up to about 550 nm. A delivery vehicle described herein can be a liposomal structure. A liposomal structure can be a vesicle in some cases. A vesicle can be unilamellar or multilamellar. Unilamellar vesicles can comprise a lipid bilayer and generally have diameters from about 50 nm to about 250 nm. Unilamellar vesicles can comprise a lipid bilayer and generally have diameters from about 50 nm, 60 nm, 70 nm, 80 nm, 90 nm, 100 nm, 110 nm, 120 nm, 130 nm, 140 nm, 150 nm, 160 nm, 170 nm, 180 nm, 190 nm, 200 nm, 210 nm, 220 nm, 230 nm, 240 nm, or up to about 250 nm.

The delivery vehicle may include a lipid structure such as a liposome, peptide lipoplex, lipid nanoparticle or other type of lipid structure.

The nanoparticle may include a liposome. A liposome can be a vesicular structure that can form via the accumulation of lipids interacting with one another in an energetically favorable manner. Liposomes can generally be formed by the self-assembly of dissolved lipid molecules, each of which can contain a hydrophilic head group and hydrophobic tails. Liposomes can consist of an aqueous core entrapped by one or more bilayers composed of natural or synthetic lipids. In some cases, liposomes can be highly reactive and immunogenic, or inert and weakly immunogenic. Liposomes composed of natural phospholipids can be biologically inert and weakly immunogenic, and liposomes can possess low intrinsic toxicity.

Unilamellar vesicles can contain a large aqueous core and can be preferentially used to encapsulate drugs. In some cases, a unilamellar vesicle can partially encapsulate a drug. Multilamellar vesicles can comprise several concentric lipid bilayers and have diameters from about 1-5 layers having outer diameters from about 1 μm, 1.5 μm, 2.0 μm, 2.5 μm, 3 μm, 3.5 μm. 4 μm, 4.5 μm, or up to 5.0 μm or greater. Liposomal structures for use with the compositions and methods herein can include a liposome, a lipoplex, or a lipopolyplex.

Lipids for Use with Delivery Vehicles. The lipids for inclusion into the delivery vehicles herein can include cationic and non-cationic lipids and can include saturated and unsaturated cationic and non-cationic lipids. In some embodiments, a delivery vehicle includes a cationic lipid. In some embodiments, a delivery vehicle includes a noncationic lipid. In some embodiments, a delivery vehicle includes both a cationic lipid and a noncationic lipid. In some embodiments, a delivery vehicle includes 1, 2, 3, 4 or more types of lipids selected from one or more of saturated cationic and unsaturated cationic and non-cationic saturated and non-cationic unsaturated lipids.

Saturated non-cationic lipids for use with the delivery vehicles herein include, for example, di-glycerol tetraether phospholipids, sphingoids, ceramides and phosphosphingolipids such as 1,2-Dialkyl-sn-glycero-3-phosphocholine, 1,2-dialkyl-sn-glycero-3-phosphoethanolamine, 1,2-Diaklyl-sn-glycero-3-phosphorylglycerol, 1,2-dialkyl-sn-glycero-3-Phosphatidylserine, 1,2-dialkyl-sn-glycero-3-Phosphate, Monoglycerol alkylate, Glyceryl hydroxyalkylate, Sorbitan monoalkylated, 1,2-dialkyl-sn-glycero-3-phosphoethanolamine-N-methyl, 1,2-dialkyl-sn-glycero-3-phosphomethanol, 1,2-dialkyl-sn-glycero-3-phosphoethanol, 1,2-dialkyl-sn-glycero-3-phosphoethanolamine-N,N-dimethyl, 1,2-dialkyl-sn-glycero-3-phosphopropanol, and 1,2-dialkyl-sn-glycero-3-phosphobutanol, where alkyl means conjugated derivatives of myristic acid, pentadecylic acid, palmitic acid, heptadecanoic acid, stearic acid, lauric acid, tridecylic acid, nonadecylic acid, arachidic acid, heneicosylic acid, behenic acid, tricosylic acid and lignoceric acid.

Unsaturated non-cationic lipids for use with the delivery vehicles herein include, for example, glycerophosphocholines, glycerophosphoethanolamines, glycerophosphoserines, glycerophosphoglycerols, glycerophosphoglycerophosphates, glycerophosphoinositols, glycerophosphoinositol monophosphates, glycerophosphoinositol bisphosphates, glycerophosphoinositol trisphosphates, glycerophosphates, glyceropyrophosphate, glycerophosphoglycerophosphoglycerols, cytidine-5-diphosphate-glycerols, glycosylglycerophospholipids, glycerophosphoinositolglycans, di-glycerol tetraether phospholipids, sphingoids, ceramides, and phosphosphingolipids, such as 1,2-Dialkyl-sn-glycero-3-phosphocholine, 1,2-dialkyl-sn-glycero-3-phosphoethanolamine, 1,2-Diaklyl-sn-glycero-3-phosphorylglycerol, 1,2-dialkyl-sn-glycero-3-Phosphatidylserine, 1,2-dialkyl-sn-glycero-3-Phosphate, Monoglycerol alkylate, Glyceryl hydroxyalkylate, Sorbitan monoalkylated, 1,2-dialkyl-sn-glycero-3-phosphoethanolamine-N-methyl, 1,2-dialkyl-sn-glycero-3-phosphomethanol, 1,2-dialkyl-sn-glycero-3-phosphoethanol, 1,2-dialkyl-sn-glycero-3-phosphoethanolamine-N,N-dimethyl, 1,2-dialkyl-sn-glycero-3-phosphopropanol and 1,2-dialkyl-sn-glycero-3-phosphobutanol, where alkyl means a conjugated derivative of oleic acid, elaidic acid, gondoic acid, erucic acid, nervonic acid, mead acid, paullinic acid, vaccenic acid, palmitoleic acid, Docosatetraenoic acid, Arachidonic acid, Dihomo-γ-linolenic acid, γ-Linolenic acid, linolelaidic acid, linoleic acid, Docosahexaenoic acid, Eicosapentaenoic acid, Stearidonic acid, and α-Linolenic acid.

Saturated cationic lipids for use with the delivery vehicles herein include, for example, those with an alkyl chain greater than 12 carbons in length, generally having a phase transition temperature greater than 20° C. and being positively charged at pH greater than about 4, such as Dimethyldioctadecylammonium, 1,2-dialkyl-sn-glycero-3-ethylphosphocholine, 1,2-dialkyl-3-dimethylammonium-propane, 1,2-dialkyl-3-trimethylammonium-propane, 1,2-di-O-alkyl-3-trimethylammonium propane, 1,2-dialkyloxy-3-dimethylaminopropane, N,N-dialkyl-N,N-dimethylammonium, N-(4-carboxybenzyl)-N,N-dimethyl-2,3-bis(alkyloxy)propan-1-aminium, 1,2-dialkyl-sn-glycero-3-[(N-(5-amino-1-carboxypentyl)iminodiacetic acid) succinyl], and N1-[2-((1S)-1-[(3-aminopropyl)amino]-4-[di(3-amino-propyl)amino]butylcarboxamido)ethyl]-3,4-di[alkyl]-benzamide, where alkyl may refer to a conjugated derivative of myristoyl, pentadecenoyl, palmitoyl, heptadecanoyl, stearoyl, lauroyl, tridecanoyl, nonadecanoyl, arachidoyl, heneicasnoyl, behenoyl, tricosanoyl and lignoceroyl.

Unsaturated cationic lipids for use with the delivery vehicles herein include, for example, cationic lipids which are not saturated and are positively charged at a pH greater than about 4, such as Dimethyldioctadecylammonium, 1,2-dialkyl-sn-glycero-3-ethylphosphocholine, 1,2-dialkyl-3-dimethylammonium-propane, 1,2-dialkyl-3-trimethylammonium-propane, 1,2-di-O-alkyl-3-trimethylammonium propane, 1,2-dialkyloxy-3-dimethylaminopropane, N,N-dialkyl-N,N-dimethylammonium, N-(4-carboxybenzyl)-N,N-dimethyl-2,3-bis(alkyloxy)propan-1-aminium, 1,2-dialkyl-sn-glycero-3-[(N-(5-amino-1-carboxypentyl)iminodiacetic acid)succinyl], N1-[2-41 S)-1-[(3-aminopropyl)amino]-4-[di(3-amino-propyl)amino]butylcarboxamido)ethyl]-3,4-di[alkyl]-benzamide, 1,2-Dialkyloxy-N,N-dimethylaminopropane, 4-(2,2-diocta-9,12-dienyl-[1,3]dioxolan-4-ylmethyl)-dimethylamine, O-alkyl ethylphosphocholines, MC3, MC2, MC4, 3β[N—(N',N'-dimethylaminoethane)-carbamoyl]cholesterol and N4-Cholesteryl-Spermine, where alkyl may refer to a conjugated derivative of oleic acid, elaidic acid, gondoic acid, erucic acid, nervonic acid, mead acid, paullinic acid, vaccenic acid, palmitoleic acid, Docosatetraenoic acid, Arachidonic acid, Dihomo-γ-linolenic acid, γ-Linolenic acid, linolelaidic acid, linoleic acid, Docosahexaenoic acid, Eicosapentaenoic acid, Stearidonic acid, and α-Linolenic acid.

A cationic lipid can be used to form a liposome. Cationic lipids may commonly attain a positive charge through one or more amines present in the polar head group. A solution of cationic lipids, often formed with neutral helper lipids, can be mixed with DNA to form a positively charged complex termed a lipoplex. Reagents for cationic lipid transfection can include N-[1-(2,3-dioleyloxy)propyl]-N,N,N-trimethylammonium chloride (DOTMA), [1,2-bis(oleoyloxy)-3-(trimethylammonio)propane] (DOTAP), 3β[N—(N',N'-dimethylaminoethane)-carbamoyl]cholesterol (DC-Chol), and dioctadecylamidoglycylspermine (DOGS). Dioleoylphosphatidylethanolamine (DOPE), a neutral lipid, may often be used in conjunction with cationic lipids because of its membrane destabilizing effects at low pH, which can aide in endolysosomal escape.

A liposome may be formed with neutral helper lipids. A liposome may be generated using cholesterol, N-[1-(2,3-dioleyloxy)propyl]-N,N,N-trimethylammonium chloride (DOTMA), [1,2-bis(oleoyloxy)-3 (trimethylammonio)propane] (DOTAP), 3β[N—(N',N'-dimethylaminoethane)-carbamoyl] cholesterol (DC-Chol), dioctadecylamidoglycylspermine (DOGS), Dioleoylphosphatidylethanolamine (DOPE), N1-[2-((1 S)-1-[(3-aminopropyl)amino]-4-[di(3-amino-propyl)amino]butylcarboxamido)ethyl]-3,4-di[oleyloxy]-benzamide (MVL5), glyceryl mono-oleate (GMO), 1,2-Distearoyl-sn-glycero-3-phosphoethanolamine (DSPE), 1,2-distearoyl-sn-glycero-3-phosphocholine (DSPC), Dimethyldioctadecylammonium (DDAB), a salt thereof, and any combination thereof. Liposomes for use with the compositions and methods herein can be found for example in PCT/US17/61111, which is incorporated herein in its entirety.

Surface Modifications of Delivery Vehicle. Lipids or liposomes or delivery vehicle of the present disclosure may be modified by a surface modification. In some cases, a surface modification to the delivery vehicles herein can be a polyethylene glycol (PEG) addition. Methods of modifying liposomal surfaces with PEG can include its physical adsorption onto a liposomal surface, its covalent attachment onto liposomes, its coating onto a liposome, or any combination thereof. In some cases, PEG can be covalently attached to a lipid particle before a liposome can be formed. A variety of molecular weights of PEG may be used. PEG can range from about 10 to about 100 units of an ethylene PEG component which may be conjugated to phospholipid through an amine group comprising or comprising about 1% to about 20%, preferably about 5% to about 15%, about 10% by weight of the lipids which are included in a lipid bilayer.

In certain cases, a nanostructure can further comprise at least one targeting agent. The term targeting agent can refer to a moiety, compound, antibody, etc. that specifically binds a particular type or category of cell and/or other particular type compounds, (e.g., a moiety that targets a specific cell or type of cell). A targeting agent can be specific (e.g., have an affinity) for the surface of certain target cells, a target cell surface antigen, a target cell receptor, or a combination thereof. In some cases, a targeting agent can refer to an agent that has a particular action (e.g., cleaves) when exposed to a particular type or category of substances and/or cells, and this action can drive the nanostructure to target a particular type or category of cell. Thus, the term targeting agent can refer to an agent that can be part of a nanostructure and plays a role in the nanostructure's targeting mechanism, although the agent itself may or may not be specific for the particular type or category of cell itself. In certain embodiments, nanostructures described herein can comprise one or more small molecule targeting agents (e.g., carbohydrate moieties). Suitable targeting agents also include, by way of non-limiting example, antibodies, antibody-like molecules, or peptides, such as an integrin-binding peptides such as RGD-containing peptides, or small molecules, such as vitamins, e.g., folate, sugars such as lactose and galactose, or other small molecules. Cell surface antigens include a cell surface molecule such as a protein, sugar, lipid or other antigen on the cell surface. In specific embodiments, the cell surface antigen undergoes internalization. Examples of cell surface antigens targeted by the targeting agents of embodiments of the present nanoparticles include, but are not limited, to the transferrin receptor type 1 and 2, the EGF receptor, HER2/Neu, VEGF receptors, integrins, NGF, CD2, CD3, CD4, CDS, CDI9, CD20, CD22, CD33, CD43, i1)38. CD56, CD69, and the leucine-rich repeat-containing G-protein coupled receptor 5 (LGR5). A targeting agent can also comprise an artificial affinity molecule, e.g., a peptidomimetic or an aptamer. Peptidomimetics can refer to compounds in which at least a portion of a peptide, such as a therapeutic peptide, is modified, and the three-dimensional structure of the peptidomimetic remains substantially the same as that of the peptide. Peptidomimetics (both peptide and non-peptidyl analogues) may have improved properties (e.g., decreased proteolysis, increased retention or increased bioavailability). Peptidomimetics generally have improved oral availability, which makes them especially suited to treatment of disorders in a human or animal. It should be noted that peptidomimetics may or may not have similar two-dimensional chemical structures but share common three-dimensional structural features and geometry.

Attachment of a targeting agent, such as an antibody, to a polymer can be achieved in any suitable manner, e.g., by any one of a number of conjugation chemistry approaches including but not limited to amine-carboxyl linkers, amine-sulfhydryl linkers, amine-carbohydrate linkers, amine-hydroxyl linkers, amine-amine linkers, carboxyl-sulfhydryl linkers, carboxyl-carbohydrate linkers, carboxyl-hydroxyl linkers, carboxyl-carboxyl linkers, sulfhydryl-carbohydrate linkers, sulfhydryl-hydroxyl tinkers, sulfhydryl-sulfhydryl linkers, carbohydrate-hydroxyl linkers, carbohydrate-carbohydrate linkers, and hydroxyl-hydroxyl linkers. In specific embodiments, "click" chemistry can be used to attach the targeting agent to the polymers of the nanoparticles provided herein. A large variety of conjugation chemistries are optionally utilized, in some embodiments, targeting agents can be attached to a monomer and the resulting compound can then be used in a polymerization synthesis of a polymer (e.g., copolymer) utilized in a nanoparticle described herein.

C. Combination Therapy

A therapeutic peptide can be administered to a subject alone or in combination with one or more other therapeutics, for example, another anti-cancer agent.

As used herein, "anti-cancer agent" refers to any drug that is effective in the treatment of malignant or cancerous disease. Non-limiting examples of major classes of anti-cancer agents include: alkylating agents, antimetabolites, natural products, or hormones, etc. Non-limiting examples of anti-cancer agents include: a chemotherapy drug, a cancer immunotherapy drug, or a photosensitizer, etc.

As used herein, the term "chemotherapy" refers to the treatment of disease by use of chemical substances, especially the treatment of cancer by cytotoxic and other drugs. Non-limiting examples of chemotherapy drugs include: an alkylating agent, an antimetabolite, an anti-tumor antibiotic, an antiviral drug, a mitotic inhibitor, or a topoisomerase inhibitor, etc. Non-limiting examples of the alkylating agent include: busulfan, carboplatin, cisplatin, cyclophosphamide, mitomycin C (MTC), or temozolamide, etc. Non-limiting examples of the antimetabolite include: 5-Fluorouracil (5-FU, FU), 6-mercaptopurine (6-MP), capecitabine (Xeloda), cytosine arabinoside (AraC), gemcitabine (dFdC), hydroxyurea (HU), or methotrexate (MTX), etc. Non-limiting examples of the anti-tumor antibiotic include Bleomycin, dactinomycin (cosmegen), or daunorubicin (cerubidine, rubidomycin), etc. Non-limiting examples of the antiviral drug include acyclovir (Acy), foscarnet (FOS), or ganciclovir (gan), etc. Non-limiting examples of the mitotic inhibitor include: demecolcine, docetaxel (taxotere), eribulin (halaven), ixabepilone (ixempra), paclitaxel (taxol), or vinblastine, etc. Non-limiting examples of the topoisomerase inhibitor include: camptothecin (CPT), etoposide (VP-16), irinotecan (camptosar), or topotecan (hycamtin), etc.

The term "immunotherapy" as used herein refers to the treatment of a disease or condition by inducing, enhancing, or suppressing an immune response. Non-limiting examples of the cancer immunotherapy drug include: a cellular immunotherapy drug, an antibody therapy drug, a cytokine therapy drug, or polysaccharide K, etc. Non-limiting examples of the cellular immunotherapy drug include: sipuleucel-T (provenge), tisagenlecleucel (kymriah), or axicabtagene ciloleucel (yescarta), etc. The term "immune checkpoint" as used herein refers to an inhibitory pathway in the immune system that is crucial for maintaining self-tolerance and modulating the duration and amplitude of physiological immune responses in peripheral tissues in order to minimize collateral tissue damage.

Non-limiting examples of antibody therapy drugs include: an anti-CD20 antibody, an anti-CD52 antibody, an anti-CTLA-4 antibody, an anti-PD-1 antibody, an anti-PD-L1 antibody, or an anti-PD-L2 antibody, etc. Non-limiting examples of cytokine therapy drugs include: IFNα, IFNβ, IFNγ, IFNγ, or IL-2, etc. Non-limiting examples of anti-CD20 antibodies include: ofatumumab (arzerra), or rituximab (rituxan, mabthera), etc. A non-limiting example of the anti-CD52 antibody is alemtuzumab (campath-1H). Non-limiting examples of the anti-PD-1 antibody include: nivolumab (opdivo), or pembrolizumab (keytruda), etc. Non-limiting examples of anti-PD-L1 antibodies include: atezolizumab (tecentriq), avelumab (bavencio), or durvalumab (imfinzi), etc. A non-limiting example of the anti-CTLA-4 antibody is ipilimumab (yervoy).

Non-limiting examples of cancers include bladder cancer, breast cancer, cervical cancer, hepatocellular carcinoma, Kaposi sarcoma, lung cancer, lymphoma, malignant melanoma, melanoma, mesothelioma, metastatic melanoma lung cancer, non-small cell lung cancer, ovarian cancer, pancreatic cancer, prostate cancer, renal cell cancer, small-cell lung cancer, or squamous lung cancer, etc. Preferably the cancer is peritoneal cancer, such as ovarian cancer.

In some embodiments, the combination therapy of the therapeutic peptide and the anti-cancer agent are administered separately. In some respects the peptide is administered first to prime the immune system before administering a second anti-cancer agent. For example, the therapeutic peptide is administered at least two weeks, at least ten days, at least one week, at least five days, at least three days, or at least one day before the administration of the second anti-cancer agent. In other aspects, administration of the peptide is continued after the administration of the second anti-cancer agent. In further aspects, administration of the peptide is concurrent to the course of administering the anti-cancer agent. In non-limiting embodiments, the administration of the peptide lasts between about 1 day to 1 year, or any time period in between, e.g., about 1 day to 10 months, about 1 week to 10 months, about 1 week to 8 months, about 1 month to 8 months, about 1 month to 6 months, about 2 months to 6 months, about 2 months to 4 months, or about 3 months, etc.

In some embodiments, the peptide and the anti-cancer agent are administered in a formulation in which the combined drugs can be administered as a single application.

III. KITS

Further disclosed herein are kits which comprise one or more therapeutic peptide(s) described herein. The therapeutic peptide may be packaged in a manner which facilitates its use to practice methods of the present disclosure. For example, a kit comprises a therapeutic peptide described herein packaged in a container with a label affixed to the container or a package insert that describes use of the therapeutic peptide in practicing the method. Suitable containers include, for example, bottles, vials, syringes, etc. The containers may be formed from a variety of materials such as glass or plastic. The container may have a sterile access port (for example the container may be an intravenous solution bag or a vial having a stopper pierceable by a hypodermic injection needle). The kit may comprise a container with a therapeutic peptide contained therein. The kit may comprise a container with (a) a therapeutic peptide as described herein and an additional therapeutic agent. An additional therapeutic agent may be an anti-cancer agent. The kit may further comprise a package insert indicating that the first and second compositions may be used to treat a particular condition such as cancer. Alternatively, or additionally, the kit may further comprise a second (or third) container comprising a pharmaceutically-acceptable buffer (e.g., bacteriostatic water for injection (BWFI), phosphate-buffered saline, Ringer's solution and dextrose solution). It may further comprise other materials desirable from a commercial and user standpoint, including, but not limited to, other buffers, diluents, filters, needles, and syringes. The therapeutic peptide may be packaged in a unit dosage form. The kit may further comprise a device suitable for administering the therapeutic peptide according to a specific route of administration or for practicing a screening assay. The kit may contain a label that describes a recommended or suggested use of the therapeutic peptide composition.

The composition comprising a therapeutic peptide(s) may be formulated in accordance with routine procedures as a pharmaceutical composition adapted for intravenous administration to mammals, such as humans, bovines, felines, canines, and murines. Typically, compositions for intravenous administration comprise solutions in sterile isotonic aqueous buffer. Where necessary, the composition may also include a solubilizing agent and/or a local anesthetic such as lignocaine to ease pain at the site of the injection. Generally, the ingredients may be supplied either separately or mixed together in unit dosage form. For example, the therapeutic peptide may be supplied as a dry lyophilized powder or water free concentrate in a hermetically sealed container such as an ampoule or sachette indicating the quantity of the therapeutic peptide. Where the composition is to be administered by infusion, it may be dispensed with an infusion bottle containing sterile pharmaceutical grade water or saline. Where the composition is administered by injection, an ampoule of sterile water for injection or saline may be provided so that the ingredients may be mixed prior to administration.

The amount of the composition described herein which will be effective in the treatment, inhibition and/or prevention of a cancer may be determined by standard clinical techniques. In addition, in vitro assays may optionally be employed to help identify optimal dosage ranges. The precise dose to be employed in the formulation may also depend on the route of administration, and the seriousness of the disease or disorder, and should be decided according to the judgment of the practitioner and each patient's circumstances. Effective doses may be extrapolated from dose-response curves derived from in vitro, animal model test systems or clinical trials.

IV. EXAMPLES

The following examples as well as the figures are included to demonstrate preferred embodiments of the invention. It should be appreciated by those of skill in the art that the techniques disclosed in the examples or figures represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

A. Materials

Cell Culture. MDA-MB-231, DU-145 and NIH-3T3 were purchased from ATCC (CRL-10317) and used within 10 passages. Cells were cultured at 37° C. and 5% CO2 (DMEM/F12 [Gibco] supplemented with 10% fetal bovine serum, Prior to the treatment with peptides, cells were serum-starved for 6 h followed by stimulation of peptides solubilized in 0.1% Fetal bovine serum for 48 h. The media was replenished every 2 d.

B. Methods

Peptide synthesis: The peptides LA-6, LA3I6, SR-8 CR-8 and RP-7 were synthesized by BIOMATIK. Briefly, the peptides were synthesized using Fmoc (N-(9-fluorenyl) methoxycarbonyl)/tBu solid-phase peptide synthesis chemistry and utilizing Fmoc-linker AM resin as support. The peptides were purified by reversed-phase preparative HPLC on a C18 column (250×4.6 mm) using an appropriate 72-28% water/acetonitrile gradient in the presence of 0.1% trifluoroacetic acid. The purified peptides were ~95% homogeneous. The molecular masses of purified peptides were determined LC/MS Agilent 6125B Single Quadrupole LC/MS. The sequence of all the peptides is given in table 1.

Cell viability assay/IC50 determination: The viability of murine NIH-3T3 cells, MDA-MB-231 and DU-145 in the presence of these peptides was determined by MTT assay. 20,000 cells/well were seeded in 96-well plates and incubated overnight in a $CO_2$ incubator for adherence. After discarding the complete media from the plate, incomplete media were added to the cells. Peptides of different concentrations were added to the wells followed by incubation for 2 h. Then 10 ml of MTT solution (5 mg/ml) was added to each well and further incubated for 3 h. Incomplete media was discarded from 96-well plates and 200 ml of DMSO was added to each well for dissolving the crystal. The well in which no peptide was added was taken as the control cells of 100% viability. Absorbance of these samples was recorded at 550 nm with an ELISA reader. The viability of the peptide-treated cells was determined with respect to the control cells of 100% viability.

Wound healing assay: The wound-healing assay on highly metastatic MDA-MB-231 cells was performed to check the anti-migratory activity of the peptides. MDA-MB-231 cells were plated in a six-well tissue culture plate to form a sub-confluent cell monolayer. The monolayer was scraped with a sterile 200 µL pipette tip in the middle of the culture well to produce equal-sized wounds. Cell debris was removed and the scratched cell monolayer was supplemented with fresh media containing sub-IC 50 concentrations of MIEN1-derived peptide and its analogs. Wound areas were measured by ImageJ software after 18 h and were compared to control.

Transwell Invasion Assay: The capacity of human breast cancer MDA-MB-231 cells to pass through a polyethylene terephthalate membrane (6.4 mm diameter; 8 m pore size) was measured using transwell chambers (Corning Life Sciences) in 24-well tissue culture plates. The MDA-MB-231 were pre-treated with the increasing concentrations of each peptide for 24 h in a 0.1% FBS containing DMEM media. Next day, cells were dislodged by trypsin and 40,000 cells/well were resuspended in a serum-free DMEM containing the second treatment of peptides and were added to the upper chamber, and 10% FBS containing media was added to the bottom chambers. After incubation for another 24 h, non-invasive cells on the upper surface of the membrane were carefully removed with a cotton swab; cells were fixed in 4% paraformaldehyde solution (Affymetrix USB) for 15 minutes followed by a PBS wash; the membrane insert was then fixed with ice-cold methanol for 20 minutes followed by staining with 0.25% crystal violet. The numbers of invaded cells were counted in random fields in Image J, and results were expressed as an average number of invaded cells compared with control.

RT-qPCR Method: The changes in the mRNA levels of various genes in response to the peptide treatment in DU-145 cells were examined. Briefly, total RNA was purified using the TRIzol reagent (Invitrogen) according to the manufacturer's instructions. 1 µg of total RNA was reverse transcribed into cDNA using the Superscript-III First-Strand Synthesis kit (Invitrogen) following the manufacturer's protocol. RT-qPCR was performed with the SYBR Green Master Mix (Invitrogen) in a Realplex2 Mastercycler ep gradient S thermal cycler (Eppendorf). The PCR program followed for all the primers was an activation at 95° C. for 15 min, followed by 40 cycles of 95° C. for 30 sec, 54° C. for 1 min, and 72° C. for 45 sec. The reaction was finally put to hold at 4 C. The primers were synthesized by Integrated DNA Technologies (Coralville, IA and are described in Table 2. 18S was used as the reference genes for the mRNA levels. Fold-expression was calculated according to the ΔΔCt method.

RNeasy Mini Kit (Cat #74106, Qiagen,) was used for RNA isolation and all procedures were performed according to the manufacturer's specification. The purification included 15 minutes of in-column DNase I (Cat #79254, Qiagen,) treatment. All RNA samples had an RNA integrity number, (RIN) in excess of 9.RNA-seq libraries were constructed at the genomics core facility at the UNT Health Science Center using the TruSeq Stranded mRNA Library Prep kit (Illumina, cat. 20020594) as per the manufacturer's instructions. The quality was controlled using Agilent Tapestation and Qubit 4 fluorometer. Sequencing was on an illumina NextSeq 550 system as per the recommended protocol. Raw sequencing files were adapter trimmed and quality filtered using fastp. The reads were mapped to hg38 reference genome using Hisat2. Differential gene expression analysis was performed using Deseq2.

TABLE 2

List of Primers Used in qPCR Study.

| Target gene | Forward primer (5' > 3') | Reverse primer (5' > 3') |
|---|---|---|
| 18S | GTAACCCGTTGAACCCCATT (SEQ ID NO: 8) | CCATCCAATCGGTAGTAGCG (SEQ ID NO: 9) |
| MMP9 | TTGACAGCGACAAGAAGTGG (SEQ ID NO: 10) | GCCATTCACGTCGTCCTTAT (SEQ ID NO: 11) |
| E-CADERIN | TGGCGTCTGTAGGAAGGCA (SEQ ID NO: 12) | GGCTCTTTGACCACCGCTCT (SEQ ID NO: 13) |
| N-CADHERIN | ACCAGGACTATGACTTGAGCC (SEQ ID NO: 14) | GGCGTGGATGGGTCTTTCA (SEQ ID NO: 15) |
| SNAIL | TCGGAAGCCTAACTACAGCGA (SEQ ID NO: 16) | AGATGAGCATTGGCAGCGAG (SEQ ID NO: 17) |
| SLUG | AAGCATTTCAACGCCTCCAAA (SEQ ID NO: 18) | GGATCTCTGGTTGTGGTATGACA (SEQ ID NO: 19) |
| ZEB1 | TGTGGTAGAAACAAATTCAGATTC (SEQ ID NO: 20) | GCCCTTCCTTTCCTGTGTCA (SEQ ID NO: 21) |

Western blot analysis: MDA-MB-231 cells and DU-145 cells were treated with all the test peptides for 48 h. Cell lysates were prepared, and cellular protein was extracted using RIPA lysis buffer (Millipore). Protein was quantified, and 40 μg of protein was separated on a 4-12% SDS-PAGE and transferred to a PVDF membrane. After blocking with 5% bovine serum albumin, the membrane was incubated with the primary antibodies specific for various proteins at 4° C. overnight. After primary antibody incubation, membrane was washed thrice in TBS containing 0.1% Tween-20 for 5 min each and then incubated with appropriate HRP-conjugated secondary antibody. The immunoreactive protein bands were visualized by enhanced chemiluminescence (ECL) on Alpha Innotech chemiluminescent detection system.

Orthotropic Breast Cancer Models in Mice: All in vivo experiments were conducted on 6-8-week-old athymic nude mice (Charles River). MDA-M13-231 ($1.5\times10^6$) cells were suspended in 50% Matrigel in DMEM high glucose (vol/vol) on ice for mammary fat pad injection. The control group received the same volume of matrigel (Corning Cat #356234) and media but no cells. After 10 days, when tumors reached an average size of ~100 mm3, mice were randomized into three groups (5 mice/group) and injected peritumorally with PBS, LA3IK, or RP-7 (30 mg/kg) on alternate days. Tumor volume was measured using a digital Vernier caliper on alternate days. The tumor volumes (mm3) were calculated using the following formula $V=(W_2\times L)/2$ (V, tumor volume: W, tumor width; L, tumor length). Mice were euthanized when rumors in the control group reached~10% of body weight. At the end of the experiment, all animals were weighed, euthanized, and liver, lung, spleen, kidney brain, and tumors were harvested. The weights of tumors and organs were recorded.

Study approval. All animal studies were performed under Institutional Animal Care and Use Committee-approved protocol at the University of North Texas Health Science Center.

Statistics: Statistical methods for RNA-seq data only were described in RNAseq method part. All data were analyzed for significance using GraphPad Prism 9.4.0 software. Representative data obtained from experiments conducted in triplicate are presented as mean±standard deviation. Data were evaluated using a Two-tailed unpaired t-test, or one-way analysis of variance (ANOVA) and Tukey's honest significant difference post hoc test, to identify statistically significant differences. A $p\text{-value}<0.05$ was regarded as statistically significant.

C. Results

Peptides design: MIEN1 contains two important functional motifs. The canonical immunoreceptor tyrosine-based activation motif (ITAM) motif is an 18-sequence amino acids (YxxI(6-8)YxxL) where tyrosine is separated from a leucine or isoleucine by any two other amino acids, giving the signature YxxL/I. This motif is essential for triggering downstream signal transduction and plays an important role in cancer cell migration and invasion. We chose a hexamer LASAVK from this conserved region to serve as a template for peptide design. Studies have shown that ACPs that contain two main biophysical parameters, viz. high hydrophobicity and cationicity can selectively kill cancer cells by interacting with anionic cell membrane components of cancer cells. To achieve that, the third-positioned serine in LA-6 was replaced with hydrophobic amino acid isoleucine to design the first analog LAIAVK.

MIEN1 also contains a functional prenylation (CAAX) motif in form of CVIL which is post-translationally modified by protein geranylgeranyltransferase-I (GGTase-I). Geranylgeranylation of MIEN1 at the CVIL motif facilitates the association of the protein to the inner leaflet of the plasma membrane, enhances migratory phenotype of cells by inducing increased filopodia formation, and potentiates directional migration. The upstream amino acids-SRPP were included in peptide design to the prenylation motif to add cationicity (from arginine) and proteolytic stability (from two prolines). A cysteine analog was also designed in which serine was replaced with cysteine. The peptides were named according to the first two amino acid resides of each peptide. The number indicated the length of the peptide.

It is well-known that cancer cells can secrete a large amount of lactate anions across plasma membranes, leading to a significant density of negative charges on the surfaces of cancer cells. Investigations have revealed that ACPs contain high hydrophobicity and a positive net charge, selectively killing cancer cells by interacting with anionic cell membrane components of cancer cells. The polar amino acids serine was replaced with hydrophobic amino acid isoleucine to design the first analog LAIAVK.

In the second design, serine was replaced by cysteine to make CRPPCVIL. In the last peptide, serine was removed to get RPPCVIL. The final peptide sequences are in Table 3

TABLE 3

Peptide sequences were designed utilizing MIENI as a template along with their biophysical parameters.

| Peptide Name: | Peptide Sequence | Charge | Molecular weight in Mass Spectra |
|---|---|---|---|
| LA-6 | LASAVK (SEQ ID NO: 3) | +1 | 629.40 |
| LA3IK | LAIAVK (SEQ ID NO: 4) | +1 | 655.60 |
| SR-8 | SRPPCVIL (SEQ ID NO: 5) | +1 | 927.10 |
| CR-8 | CRPPCVIL (SEQ ID NO: 6) | +1 | 939.35 |
| RP-7 | RPPCVIL(SEQ ID NO: 7) | +1 | 836.50 |

The MIEN1-derived Peptide RP-7 and its analog LA3IK suppresses Migration and invasion of MDA-MB-231 Cancer Cells: MIEN1 protein is known to play a critical role in migration, invasion and proliferation of various types of cancer cell lines. Cell invasion and migration are crucial steps in the progression of tumor metastasis. We performed wound healing and transwell migration assays on human breast cancer MDA-MB-231 cells with all the native peptides and the analogs of MIEN1. LA3IK and RP-7 showed a significantly reduced number of migrated cells in the wound healing assay in a dose-dependent manner. In addition to cell migration, we have also observed a considerable decrease in the number of invaded cells in LA3IK and RP-7 treated MDA-MB-231 cells in a dose-dependent manner. Thus, these compounds significantly inhibited cell migration and invasion at concentrations where no significant antiproliferative and proapoptotic effects were observed in cell viability assays.

LA3IK and RP-7 inhibit the proteins involved in cancer cell migration: To elucidate mechanisms of peptide-induced inhibition of MIEN1 signaling pathways in different cancer cells, we examined signal transduction events following the peptide exposure in MDA-MB-231 and DU-145 prostate cancer cells. Prenylated MIEN1 associates with the inner leaflet of the plasma membrane and mediate signaling through the Akt/NF-κB axis to influence the gene expression for cell migration and invasion. It also enhances F-actin polymerization through the cofilin and focal adhesion kinase (FAK) pathways. MIEN1 promotes cellular adhesion and actin dynamics by inducing phosphorylation of FAK at Tyr-925 and reducing cofilin phosphorylation at Ser-3, which results in breast cancer cell migration. We started our investigation by examining the status of the proteins activated by MIEN1 in the western blot experiments.

Interestingly, the phosphorylation of focal adhesion kinase (FAK) at key tyrosine 925 was inhibited by LA3IK and RP-7 treated MDA-MB-231 cell lysates, indicating an inhibition of a major protein in the MIEN1 signaling pathways. The actin dynamics regulated by MIEN1 to facilitate migration were also overturned by LA3IK and RP-7 as the accumulation of phosphorylated cofilin (inactive cofilin) was observed in peptide-treated whole cell lysates of MDA-MB-231 and DU-145 cells. The phosphorylation of src at tyrosine 416 was also inhibited by LA3IK and RP-7 which downregulated the kinase activity of src.

LA3Ik and RP-6 inhibit the proteins involved in cancer cell migration: Malignant progression and cancer metastasis are strongly correlated with the ability of cancer cells to migrate. The drugs which are able to inhibit this first step could be lead molecules for the future. To elucidate mechanisms of Peptide-induced inhibition of MEIN1 signaling pathways in different cancer cells, we examined signal transduction events following all the peptide exposure in MDA-MB-23cells, Both LA3IK and RP-7 were able to inhibit the signaling proteins responsible for migration. We observed a marked inhibition of phosphor FAK and phospho src in LA31K and RP-7 treated cells which play a key role in the migration of breast cancer cells (FIG. 4).

We also observed an increase in phospho-cofilin which further reduces the migratory ability of MDA-MB-231 cells. Interestingly these are key proteins that are regulated by MIEN1 to cause migration and invasion. The inhibition of the phosphorylated states of these proteins indicates that the peptides were very specific to the MIEN1 signaling pathways.

LI3K and RP-6 Peptide-treated cells reverse the EMT markers in DU-145 Prostate cancer cells: Epithelial to mesenchymal transition (EMT) activation results in cancer cells acquiring mesenchymal and stem cell properties also confer a drug-resistant phenotype. Cells that have undergone EMT lose adherent junctions due to both transcriptional repression of E-cadherin and the elimination of cell-surface E-cadherin with a concomitant increase of mesenchymal markers, such as N-cadherin. The EMT sequences occur under a transcriptional control with Slug and SNAIL, ZEB1 etc.

The EMT reversal function of LA3IK and RP-7 was studied by qPCR where there was a significant decrease in the gene expression of SLUG, SNAIL, MMP 9, N-Cadherin and Zeb-1 with a concomitant increase in the epithelial marker E-Cadherin.

Administration of LA3IK and RP-7 doses reduced tumor burden in an orthotopic model of breast cancer in athymic nude mice: To check the in vivo anti-tumor activity of both LA3IK and RP-7 in a preclinical model, we injected these peptides into a group of mice bearing tumors grown from TNBC MDA-MB-231 cells. In this model, MDA-MB-231 tumor cells were inoculated into the mammary fat pads of female mice, and when the tumors became palpable, treatment started with LA3IK and RP-7 at 30 mg/Kg on alternate days. The results showed that LA3IK inhibited the growth of MDA-MB-231 tumors in athymic nude as indicated by a decrease in the tumor volume. The in vivo effectiveness was comparatively lesser for RP-7. However, the overall tumor size was significantly lesser than the untreated mice group. The results showed that while there was robust tumor growth in the untreated group, the LA3IK and RP-7 were quite effective in suppressing tumor growth in mice which is an indicator of their therapeutic potential. Tumor measurements showed a decrease of 75.39% of tumor volume in LA3IK treated mice group which qualifies as partial response (P.R.) of human tumor equivalent as per the Response Evaluation Criteria in Solid Tumors (RECIST) RP-7 also showed 37.43% decrease in tumor volume. LA3IK and RP-7 peptides were well-tolerated by athymic mice at a very high dose of 90 mg/Kg. No significant toxicity or death was noted for all the treated m ice. In another experiment, two groups of mice received three times the experimental dose of both the peptides at 90 mg/Kg on Day 5 and Day 15 to check for potential toxicity. The mice did not display any signs of toxicity and were alive on the termination day of the experiment.

Example 2

Peptide stability is a critical aspect in the development of therapeutic agents, and a promising approach to enhancing peptide stability is replacing L-amino acids with their D-enantiomers. This enantiomeric substitution involves using mirror-image counterparts of the naturally occurring L-amino acids. The incorporation of D-amino acids can impart increased resistance to enzymatic degradation, rendering the peptide less susceptible to proteolysis and prolonging its half-life in biological systems. Moreover, the chiral difference in D-amino acids can hinder recognition by proteolytic enzymes, contributing to the peptide's overall stability. By strategically substituting specific L-amino acids with their D-form counterparts, peptides can be created with improved stability, opening new avenues for the development of more effective and long-lasting therapeutic interventions. The L-amino acids have been substituted in LA3IK and RP-7 with the D-isomers to enhance the stability and anti-cancer properties of the two peptides.

| Peptide Name: | Peptide Sequence | Charge | Molecular Weight in Mass Spectra |
|---|---|---|---|
| LA3IK | LAIAVK (SEQ ID NO: 4) | +1 | 655.60 |
| D-LA3IK | d(L)d(A)d(I)d(A)d(V)d(K) (SEQ ID NO: 9) | +1 | 655.60 |
| RP-7 | RPPCVIL(SEQ ID NO: 8) | +1 | 836.50 |
| D-RP-7 | d(R)d(P)d(P)d(C)d(V)d(I)d(L) (SEQ ID NO: 10) | +1 | 836.50 |
| LA3IK Scrambled | LAKAVI (SEQ ID NO: 11) | +1 | 655.60 |
| RP-7 Scrambled | RPPCVIL(SEQ ID NO: 8) | +1 | 836.50 |

Analytical LC-MS/MS conditions. Levels of (D/L)-LA3IK and (D/L)-RP-7 for in vitro and in vivo pharmacology assays were monitored by LC-MS/MS using a Sciex (Framingham, MA) 6500 QTRAP® mass spectrometer coupled to a Shimadzu (Columbia, MD) Nexera LC. The compound was detected with the mass spectrometer in positive MRM (multiple reaction monitoring) mode by following the precursor to fragment ion transition 655.3 to 411.3 (LA3IK), 838.6 to 640.4 (RP-7). An Agilent Poroshell 120 EC-C18 column (2.7 micron, 50×3.0 mm) was used for chromatography with the following conditions: Buffer A: dH20+10% acetonitrile, 0.1% formic acid and 2 mM ammonium acetate, Buffer B: dH2O+90% acetonitrile, 0.1% formic acid and 2 mM ammonium acetate; 0-0.5 min 3% B, 0.5-3.0 min gradient to 100% B, 3.0-3.5 min hold 100% B, 3.5-3.51 min gradient to 3% B, 3.51-4.5 hold 3% B. Tolbutamide (transition 271.2.2 to 91.2 from Sigma (St. Louis, MO) was used as an internal standard (IS).

Figure 12:
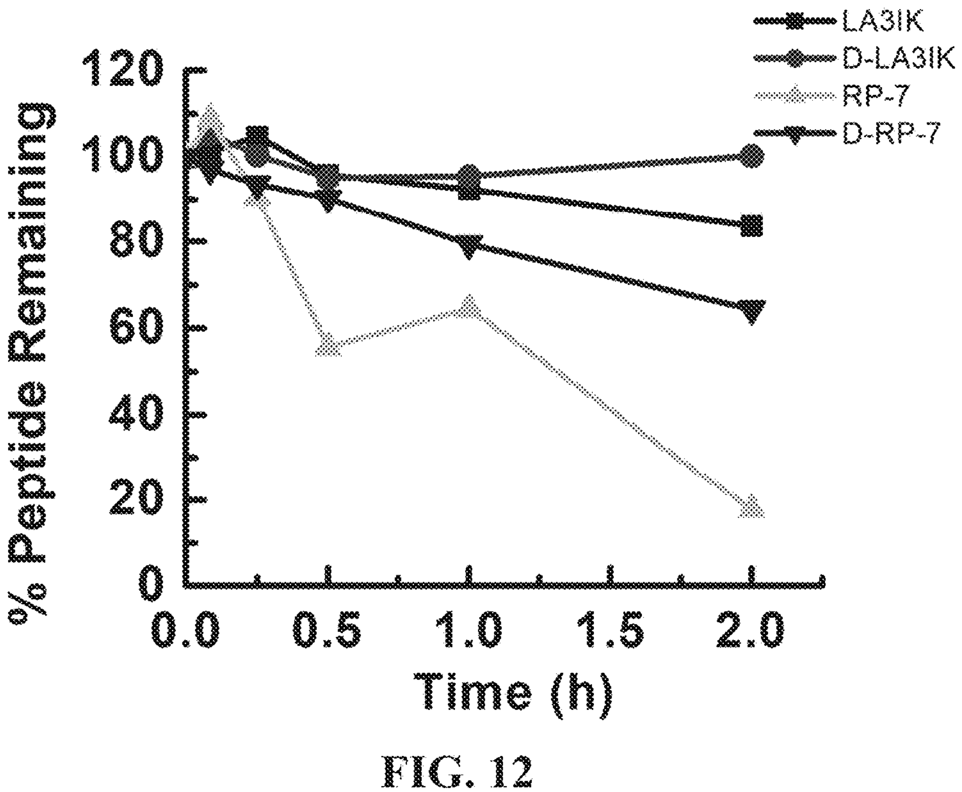
FIG. 12. Liver Microsomal stability assay of LA3IK, D-LA3IK, RP-7 and D-RP-7.

Mouse liver microsome stability. Male ICR/CD-1 mouse microsome fractions (lot 2110330) were purchased from Xenotech (Kansas City, KS). Microsome protein (0.5 mg/mL) was placed in a glass screw cap tube; a 2 mM DMSO stock of (D/L)-LA3IK and (D/L)-RP-7 were spiked into separate 50 mM Tris, pH 7.5 solution and this was added to the microsome solution on ice. The final concentration of compounds after addition of all reagents was 2 μM. An NADPH-regenerating system (1.7 mg/ml NADP, 7.8 mg/ml glucose-6-phosphate, 6 U/ml glucose-6-phosphate dehydrogenase in 2% w/v $NaHCO_3$/10 mM $MgCl_2$) was added for analysis of Phase I metabolism after heating both the regenerating solution and the sample tubes to 37° C. for 5 min in a 37° C. shaking water bath. The incubation was continued and at varying time points after addition of phase I cofactors, the reaction was stopped by the addition of 0.5 ml of acetonitrile containing IS and formic acid such that the final concentration of IS was 100 ng/ml and acid was 0.1%. Time 0 samples were stopped with the acetonitrile solution while still on ice prior to addition of the NADPH regenerating system and compound, which were subsequently added. The samples were incubated 10' at RT and then spun at 16,100×g for 5 min in a microcentrifuge at 4° C. The supernatant was analyzed by LC-MS/MS. The method described in McNaney, et al was used with modification for determination of metabolic stability half-life by substrate depletion. A "% remaining" value was used to assess metabolic stability of a compound over time. The LC-MS/MS peak area of the incubated sample at each time point was divided by the LC-MS/MS peak area of the time 0 (TO) sample and multiplied by 100. The natural Log (LN) of the % remaining of compound was then plotted versus time (in min) and a linear regression curve plotted going through y-intercept at LN(100). The half-life (T ½) was calculated as T ½=0.693/slope. The liver microsomal stability data is shown in FIG. 12.

Plasma Stability. CD1 mouse plasma isolated using acidified citrate dextrose (ACD) was purchased from BioIVT and a DMSO stock of each compound was diluted into it at a final concentration of 2 μM. An aliquot was immediately removed for a zero time point and quenched with an equal volume of acetonitrile containing 0.2% formic acid and 200 ng/ml Tolbutamide IS. The remainder of the sample was incubated in a 37° C. water bath for up to 24 hours. Samples were removed at the indicated times and processed as described for the zero time point. After vortexing and centrifugation to pellet protein, the supernatant was analyzed by LC-MS/MS as described above. A control incubation was conducted in saline (0.9% NaCl).

Figures 13A, 13B:
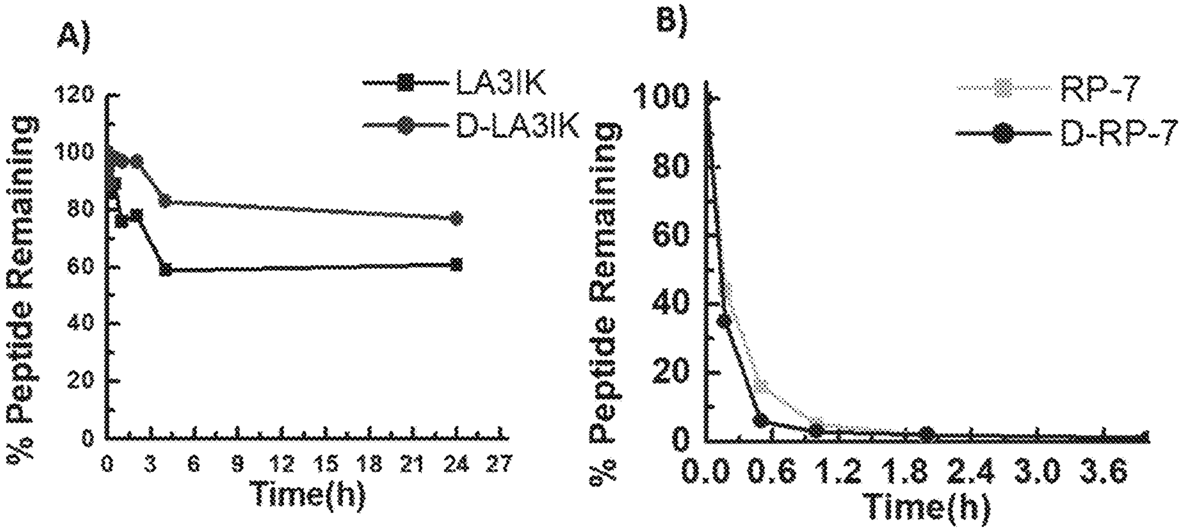
FIG. 13A-13B. Plasma stability assay of (A) LA3IK and D-LA3IK, (B) RP-7 and D-RP-7.

The plasma stability data is shown in FIG. 13. The half-life of all four peptides has been provided in Table 4 and the pharmacokinetic properties of D-LA3IK and D-RP-7 were reported in Table 5.

TABLE 4

Half-life of D and L isomers of D-LA3IK and RP-7 in mouse liver microsomes and murine plasma.

| | Mouse Microsome $T_{1/2}$ (min) | Murine Plasma $T_{1/2}$ (min) |
|---|---|---|
| LA3IK | >120 | 153 |
| D-LA3IK | >120 | >1440 |
| RP-7 | 52.3 | 18 |
| D-RP-7 | >120 | 7 |

TABLE 5

Pharmacokinetic parameters in CD-1 female mice intravenous injections 5 mg/kg.

| | D-LA3IK | D-RP-7 |
|---|---|---|
| Terminal $T_{1/2}$ (min) | 215 | 830 |
| Tmax (min) | 5 | 5 |
| Cmax (ng/ml) | 3574 | 48 |
| $AUC_{last}$ (min*ng/ml) | 203,986 | 2634 |
| Vss (mL/kg) | 1574 | 1,310,506 |
| Cl (mL) | 24.5 | 1415.5 |

Figures 14A, 14B:
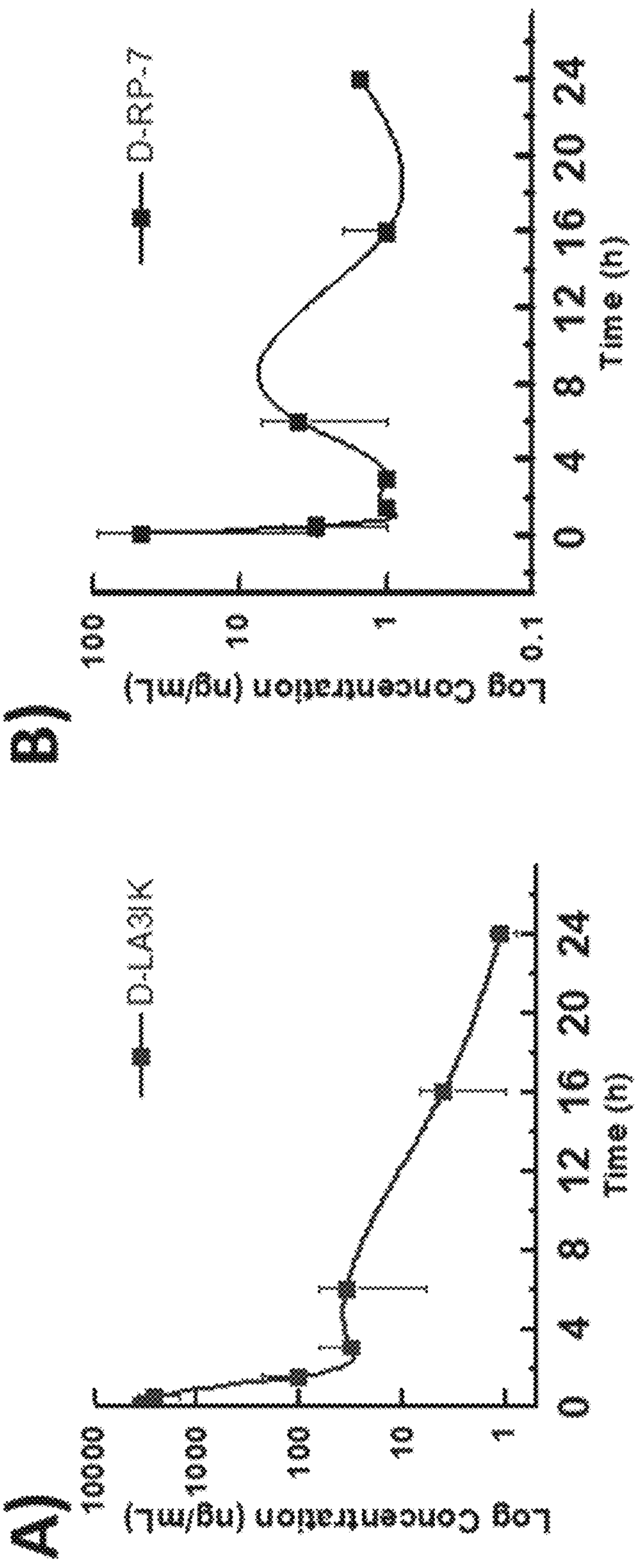
FIG. 14A-14B. Pharmacokinetic Plot of D-LA3IK and RP-7 in the mouse plasma over time. When in CD-1 Female Mice were given intravenous injections of 5 mg/kg (A) D-LA3IK and (B) RP-7.

Pharmacokinetic studies. Pharmacokinetic studies for the D isomers of LA3IK and RP-7 were performed by dosing 6-week-old CD1 mice (Charles River, Wilmington, MA) with each compound by the indicated routes at 8-10 ml/kg formulated in 100% D5W. Animals were sacrificed in groups of three, blood was obtained by a submandibular puncture at each time point into $K_2$EDTA tubes and plasma isolated by centrifugation at 9600×g for 10 min. Fifty μl of plasma was mixed with a 3× volume of acetonitrile containing formic acid and tolbutamide IS. The samples were vortexed 15 sec, incubated at room temp for 10' and spun twice at 16,100×g 4° C. in a refrigerated microcentrifuge. The resulting supernatants were evaluated by LC-MS/MS as described above. Standard curves were generated using blank plasma (Bioreclamation, Westbury, NY) spiked with known concentrations of compound and processed as described above. The concentrations of drug in each time-point sample were quantified using Analyst software (Sciex). Compounds were assumed to partition equally between red blood cells and plasma. A value of 3-fold above the signal obtained from blank plasma was designated the limit of detection (LOD). The limit of quantitation (LOQ) was defined as the lowest concentration at which back calculation yielded a concentration within 20% of theoretical. Terminal half-life (T½), area under the concentration time curve (AUC), volume of distribution at steady state (Vss), and clearance (Cl) values were calculated using the noncompartmental analysis tool of Phoenix WinNonLin 64 (version 8.3.3.33, Certara/Pharsight, Sunnyvale, CA). The in vivo peptide concentrations are shown in FIG. 14.

Figure 15:
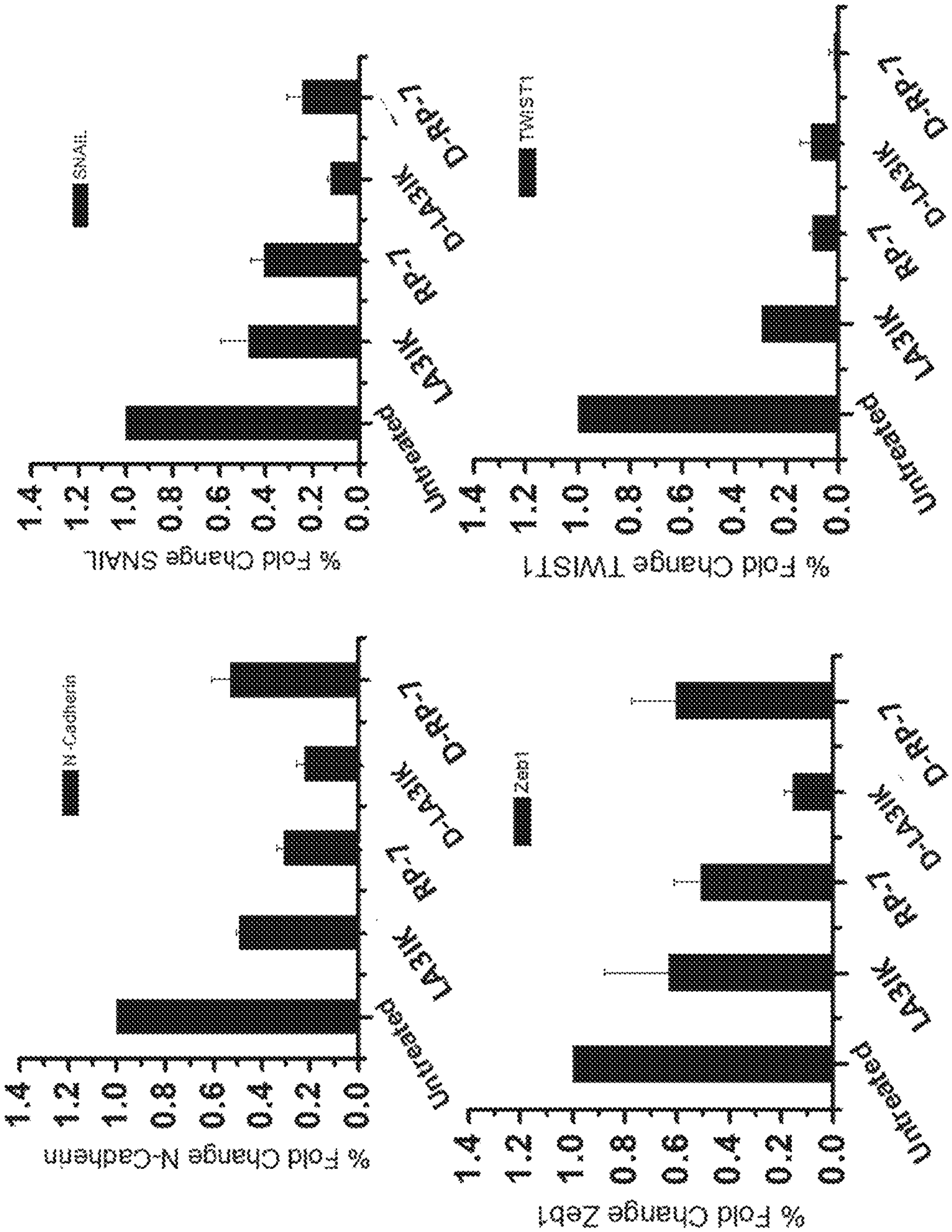
FIG. 15. Quantitative real-time PCR analysis of different EMT genes in MDA-MB-231cells after peptide treatment. Changes in the mRNA expression levels of EMT-related genes were evaluated using real-time RT-PCR after 48 h treatment with all peptides.
Figure 16:
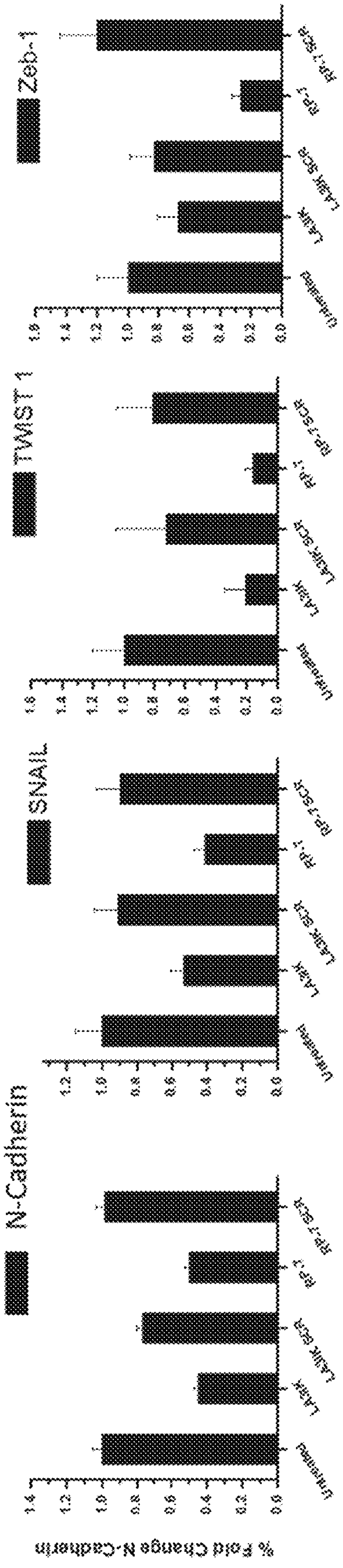
FIG. 16. Quantitative real-time PCR analysis of different EMT genes in MDA-MB-231cells after LA3IK and RP-7 treatments in comparison with LA3IK SCR and RP-7 SCR.

RT-PCR Method. Changes in the mRNA levels of various genes in both L and D isomers of LA3IK and RP-7 in response to the peptide treatment on MDA-MB-231 was determined by RT-PCR. Total RNA was extracted using the TRIzol reagent (Invitrogen) 1 μg of total RNA was used for cDNA reverse transcription using the Superscript-III First Strand Synthesis kit (Invitrogen) following the manufacturer's protocol. All real-time PCR reactions were performed in duplicates in a 20 μl volume using SYBR Green Master Mix (Invitrogen) in a Realplex2 Mastercycler ep gradient S thermal cycler (Eppendorf). The PCR program followed for all the primers was an activation at 95° C. for 15 min, followed by 40 cycles of 95° C. for 30 sec, 54° C. for 1 min, and 72° C. for 45 sec. The reaction was finally put to hold at 4° C. 18S was used as the reference gene for the mRNA levels. Relative change in gene expression was calculated according to the ΔΔCt method. The qPCR data is shown in FIG. 15 and FIG. 16.

Figure 17:
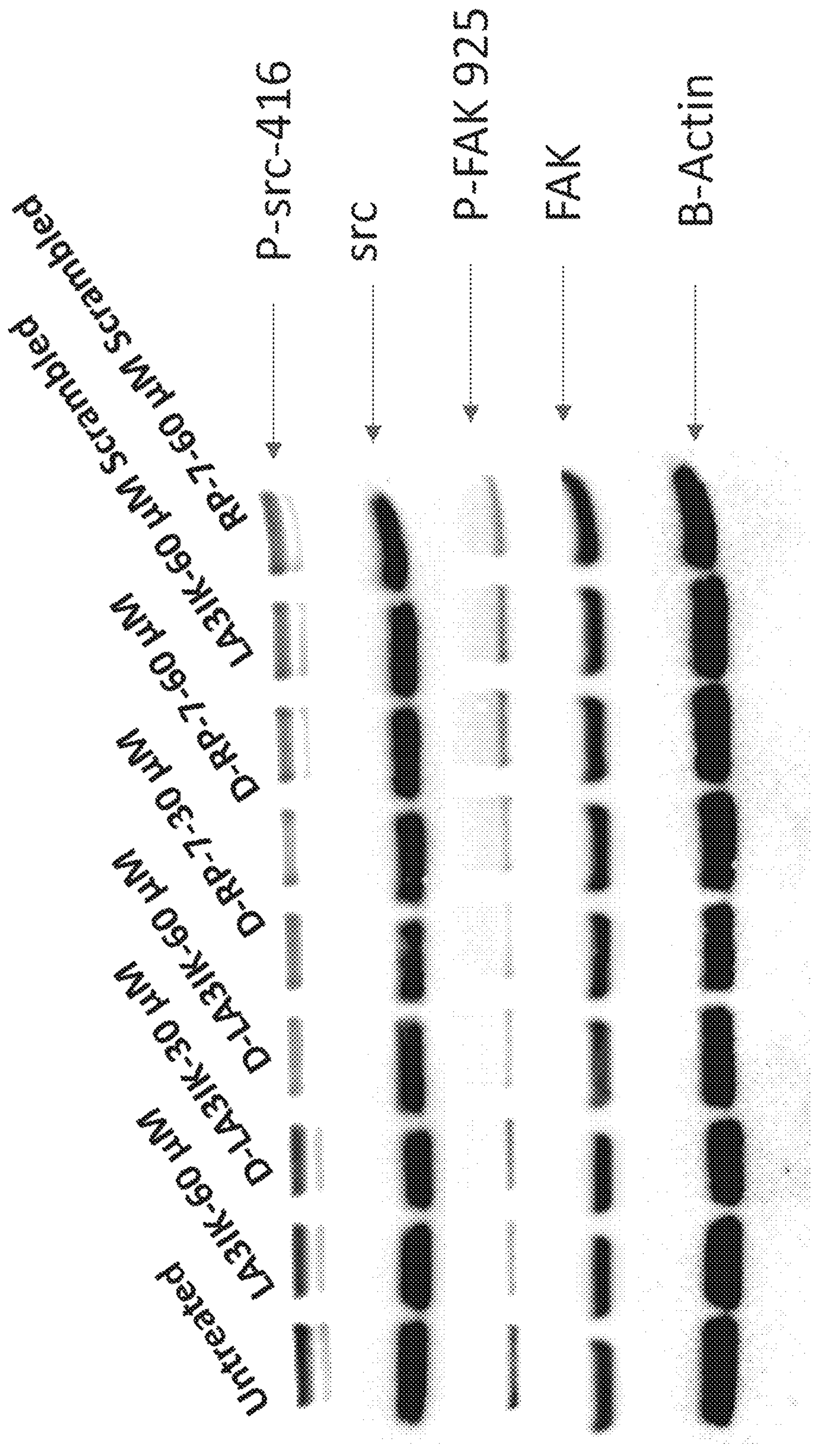
FIG. 17. Western Blot of D and L isomers of LA3IK, RP-7 and the scrambled L isomers of LA3IK and RP-7. MDA-MB-231 Cells were exposed to the peptides at 90 μM for 48 h and subjected to Western blot analysis with the indicated antibodies. β-actin was used as a loading control.

Western blot analysis. Western blot analysis was performed according to standard protocols. MDA-MB-231 cells were treated with LA3IK, D-LA3IK, RP-7 and D-RP-7 for 48 h. Cell lysates were made in RIPA lysis buffer and followed with protein quantification. 40 μg of total protein was separated on a 4-12% precast polyacrylamide gel and subsequently transferred to a PVDF membrane. Protein blocking was done with 5% bovine serum albumin, and the membrane was incubated with primary antibodies specific for various proteins at 4° C. for 8-10 hours. Afterward, the membrane was washed three times in TBST and then incubated with the appropriate secondary antibody. The protein bands were visualized on Alpha Innotech chemiluminescent detection system. The scrambled peptides where the amino acid positions were swapped were less active than the D-LA3IK and D-RP-7 at the same concentrations. The images of the western blot are shown in FIG. 17.

SEQUENCE LISTING

```
Sequence total quantity: 22
SEQ ID NO: 1            moltype = AA  length = 115
FEATURE                 Location/Qualifiers
source                  1..115
                        mol_type = protein
                        organism = Homo sapiens
SEQUENCE: 1
MSGEPGQTSV APPPEEVEPG SGVRIVVEYC EPCGFEATYL ELASAVKEQY PGIEIESRLG  60
GTGAFEIEIN GQLVFSKLEN GGFPYEKDLI EAIRRASNGE TLEKITNSRP PCVIL       115

SEQ ID NO: 2            moltype = AA  length = 116
FEATURE                 Location/Qualifiers
source                  1..116
                        mol_type = protein
                        organism = Homo sapiens
SEQUENCE: 2
MSGEPGQTSV APPPEEVEPG SGVRIVVEYC EPCGFEATYL ELASAVKEQY PGIEIESRLG  60
GTGAFEIEIN GQLVFSKLEN GGFPYEKDVS IYSVGRTSWS PYPNSASSCH STPLAH      116

SEQ ID NO: 3            moltype = AA  length = 6
FEATURE                 Location/Qualifiers
REGION                  1..6
                        note = synthetic peptide
source                  1..6
                        mol_type = protein
                        organism = synthetic construct
SEQUENCE: 3
LASAVK                                                             6

SEQ ID NO: 4            moltype = AA  length = 6
FEATURE                 Location/Qualifiers
REGION                  1..6
                        note = synthetic peptide
source                  1..6
                        mol_type = protein
                        organism = synthetic construct
```

```
SEQUENCE: 4
LAIAVK                                                      6

SEQ ID NO: 5           moltype = AA  length = 8
FEATURE                Location/Qualifiers
REGION                 1..8
                       note = synthetic peptide
source                 1..8
                       mol_type = protein
                       organism = synthetic construct
SEQUENCE: 5
SRPPCVIL                                                    8

SEQ ID NO: 6           moltype = AA  length = 8
FEATURE                Location/Qualifiers
REGION                 1..8
                       note = synthetic peptide
source                 1..8
                       mol_type = protein
                       organism = synthetic construct
SEQUENCE: 6
CRPPCVIL                                                    8

SEQ ID NO: 7           moltype = AA  length = 7
FEATURE                Location/Qualifiers
REGION                 1..7
                       note = synthetic peptide
source                 1..7
                       mol_type = protein
                       organism = synthetic construct
SEQUENCE: 7
RPPCVIL                                                     7

SEQ ID NO: 8           moltype = DNA  length = 20
FEATURE                Location/Qualifiers
misc_feature           1..20
                       note = synthetic oligonucleotide
source                 1..20
                       mol_type = other DNA
                       organism = synthetic construct
SEQUENCE: 8
gtaacccgtt gaaccccatt                                       20

SEQ ID NO: 9           moltype = DNA  length = 20
FEATURE                Location/Qualifiers
misc_feature           1..20
                       note = synthetic oligonucleotide
source                 1..20
                       mol_type = other DNA
                       organism = synthetic construct
SEQUENCE: 9
ccatccaatc ggtagtagcg                                       20

SEQ ID NO: 10          moltype = DNA  length = 20
FEATURE                Location/Qualifiers
misc_feature           1..20
                       note = synthetic oligonucleotide
source                 1..20
                       mol_type = other DNA
                       organism = synthetic construct
SEQUENCE: 10
ttgacagcga caagaagtgg                                       20

SEQ ID NO: 11          moltype = DNA  length = 20
FEATURE                Location/Qualifiers
misc_feature           1..20
                       note = synthetic oligonucleotide
source                 1..20
                       mol_type = other DNA
                       organism = synthetic construct
SEQUENCE: 11
gccattcacg tcgtccttat                                       20

SEQ ID NO: 12          moltype = DNA  length = 19
FEATURE                Location/Qualifiers
misc_feature           1..19
                       note = synthetic oligonucleotide
```

```
source                  1..19
                        mol_type = other DNA
                        organism = synthetic construct
SEQUENCE: 12
tggcgtctgt aggaaggca                                                        19

SEQ ID NO: 13           moltype = DNA  length = 20
FEATURE                 Location/Qualifiers
misc_feature            1..20
                        note = synthetic oligonucleotide
source                  1..20
                        mol_type = other DNA
                        organism = synthetic construct
SEQUENCE: 13
ggctctttga ccaccgctct                                                       20

SEQ ID NO: 14           moltype = DNA  length = 21
FEATURE                 Location/Qualifiers
misc_feature            1..21
                        note = synthetic oligonucleotide
source                  1..21
                        mol_type = other DNA
                        organism = synthetic construct
SEQUENCE: 14
accaggacta tgacttgagc c                                                     21

SEQ ID NO: 15           moltype = DNA  length = 19
FEATURE                 Location/Qualifiers
misc_feature            1..19
                        note = synthetic oligonucleotide
source                  1..19
                        mol_type = other DNA
                        organism = synthetic construct
SEQUENCE: 15
ggcgtggatg ggtctttca                                                        19

SEQ ID NO: 16           moltype = DNA  length = 21
FEATURE                 Location/Qualifiers
misc_feature            1..21
                        note = synthetic oligonucleotide
source                  1..21
                        mol_type = other DNA
                        organism = synthetic construct
SEQUENCE: 16
tcggaagcct aactacagcg a                                                     21

SEQ ID NO: 17           moltype = DNA  length = 20
FEATURE                 Location/Qualifiers
misc_feature            1..20
                        note = synthetic oligonucleotide
source                  1..20
                        mol_type = other DNA
                        organism = synthetic construct
SEQUENCE: 17
agatgagcat tggcagcgag                                                       20

SEQ ID NO: 18           moltype = DNA  length = 21
FEATURE                 Location/Qualifiers
misc_feature            1..21
                        note = synthetic oligonucletotide
source                  1..21
                        mol_type = other DNA
                        organism = synthetic construct
SEQUENCE: 18
aagcatttca acgcctccaa a                                                     21

SEQ ID NO: 19           moltype = DNA  length = 23
FEATURE                 Location/Qualifiers
misc_feature            1..23
                        note = synthetic oligonucleotide
source                  1..23
                        mol_type = other DNA
                        organism = synthetic construct
SEQUENCE: 19
ggatctctgg ttgtggtatg aca                                                   23

SEQ ID NO: 20           moltype = DNA  length = 24
FEATURE                 Location/Qualifiers
```

-continued

```
misc_feature          1..24
                      note = synthetic oligonucleotide
source                1..24
                      mol_type = other DNA
                      organism = synthetic construct
SEQUENCE: 20
tgtggtagaa acaaattcag attc                                24

SEQ ID NO: 21         moltype = DNA  length = 20
FEATURE               Location/Qualifiers
misc_feature          1..20
                      note = synthetic oligonucleotide
source                1..20
                      mol_type = other DNA
                      organism = synthetic construct
SEQUENCE: 21
gcccttcctt tcctgtgtca                                     20

SEQ ID NO: 22         moltype = AA  length = 7
FEATURE               Location/Qualifiers
source                1..7
                      mol_type = protein
                      organism = synthetic construct
SEQUENCE: 22
ILEAIRR                                                   7
```

The invention claimed is:

1. A peptide consisting of an amino acid sequence selected from SEQ ID NO: 4 and SEQ ID NO: 7, wherein the peptide binds to Migration and Invasion Enhancer 1 (MIEN1) and inhibits MIEN1-mediated intracellular signaling.

2. A composition comprising a peptide consisting of the amino acid sequence of SEQ ID NO: 4, a peptide consisting of the amino acid sequence of SEQ ID NO: 7, or both peptides, and a pharmaceutically acceptable carrier or delivery vehicle, wherein the peptide(s) bind to Migration and Invasion Enhancer 1 (MIEN1) and inhibit MIEN1-mediated intracellular signaling.

3. A conjugate comprising a peptide consisting of an amino acid sequence selected from SEQ ID NO: 4 and SEQ ID NO: 7, coupled to a targeting agent or a tag, wherein the peptide binds to Migration and Invasion Enhancer 1 (MIEN1) and inhibits MIEN1-mediated intracellular signaling, coupled to a targeting agent or a tag wherein the tag is selected for Hexahistidine (6×His), Glutathione S transferase (GST) or an antibody epitope.

4. The conjugate of claim 3, wherein the peptide is covalently coupled to the targeting agent or the tag.

5. The composition of claim 2, wherein the delivery vehicle is a nanoparticle or a liposome.

6. The peptide of claim 1, wherein one or more amino acids of the peptide is a D-amino acid.

7. A method for treating a subject having a cancer selected from breast cancer, prostate cancer, colorectal cancer, gastric cancer, ovarian cancer, squamous cell carcinoma, and non-small cell lung cancer, comprising administering to the subject the peptide of claim 1.

8. The method of claim 7, further comprising administering a chemotherapy drug or a cancer immunotherapy drug to the subject wherein the chemotherapy drug or the cancer immunotherapy drug is administered sequentially or concurrently with the peptide.

9. A method for inhibiting cancer migration or invasion in a subject having a cancer selected from breast cancer, prostate cancer, colorectal cancer, gastric cancer, ovarian cancer, squamous cell carcinoma, and non-small cell lung cancer, comprising administering the peptide of claim 1.

10. The method of claim 9, further comprising administering at least one chemotherapy drug or a cancer immunotherapy drug to the subject, wherein the chemotherapy drug or the cancer immunotherapy drug is administered sequentially or concurrently with the peptide.

11. A method of inhibiting MIEN1-mediated cancer cell signaling in a subject, comprising administering to the subject the composition of claim 2, wherein the method results in decreased phosphorylation of focal adhesion kinase (FAK), decreased phosphorylation of SRC, and increased phosphorylation of cofilin.

* * * * *